(12) United States Patent
Matsumoto

(10) Patent No.: US 6,280,587 B1
(45) Date of Patent: Aug. 28, 2001

(54) ENZYME ELECTRODE AND A BIOSENSOR AND A MEASURING APPARATUS THEREWITH

(75) Inventor: Toru Matsumoto, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/345,410

(22) Filed: Jul. 1, 1999

(30) Foreign Application Priority Data

Jul. 2, 1998 (JP) .................................................. 10-187528
Jul. 2, 1998 (JP) .................................................. 10-187529

(51) Int. Cl.$^7$ .................................................. G01N 27/26
(52) U.S. Cl. .......................... 204/403; 204/418; 205/317; 427/2.13
(58) Field of Search ................................. 204/403, 418, 204/415; 427/2.13; 205/317, 316

(56) References Cited

FOREIGN PATENT DOCUMENTS

| 56-73342 | 6/1981 | (JP) . |
| 59-22620 | 2/1984 | (JP) . |
| 62-144062 | 6/1987 | (JP) . |
| 3-72254 | 3/1991 | (JP) . |
| 6-141889 | 5/1994 | (JP) . |
| 8-50112 | 2/1996 | (JP) . |
| 10-26601 | 1/1998 | (JP) . |

*Primary Examiner*—T. Tung
*Assistant Examiner*—Alex Noguerola
(74) *Attorney, Agent, or Firm*—Young & Thompson

(57) ABSTRACT

On an insulating substrate 1 is formed an electrode 2 as a working electrode, on which is formed a binding layer 3 mainly consisting of γ-aminopropyltriethoxysilane. On the binding layer are sequentially formed an immobilized enzyme layer 4 in which a catalytic enzyme is immobilized in an organic polymer and a permeation restricting layer 5.

53 Claims, 31 Drawing Sheets

(a)

A-A' CROSS SECTION (b)

(a)

(b)

(a)

(b)

B-B' CROSS SECTION    A-A' CROSS SECTION (b)　　　　　　　　(c)

Urea layer

Acetylcellulose layer

A−A' CROSS SECTION (a)          (b)

(a)

B-B' CROSS SECTION    A-A' CROSS SECTION (b)                           (c)

ENZYME ELECTRODE AND A BIOSENSOR AND A MEASURING APPARATUS THEREWITH

REFERENCE TO RELATED APPLICATION AND INCORPORATION BY REFERENCE

This application is based on applications NO.HEI10-187528 filed in Japan and NO.HEI10-187529 filed in Japan, the content of which is incorporated hereinto by reference.

BACKGROUND OF THE INVENTION

1. Field of the Invention

This invention relates to an enzyme electrode for electrochemically determining a particular chemical substance in a solution via an enzyme reaction as well as a biosensor and a measuring apparatus therewith.

2. Description of the Related Art

A process employing an enzyme reaction in combination with an electrochemical reaction has been extensively used for determining a variety of components in, for example, a biological sample. For instance, there has been commonly used a biosensor in which by the catalytic action of an enzyme, a chemical compound in a solution is converted into hydrogen peroxide, which is then determined via an oxidation-reduction reaction. For example, a glucose biosensor can quantify an amount of glucose in a sample by oxidizing glucose with glucose oxidase (GOX) into gluconolactone and hydrogen peroxide, and determining the amount of the hydrogen peroxide because it is proportional to the glucose concentration.

Such a type of sensor generally has a layer restricting permeation of a target chemical compound (hereinafter, referred to as a "permeation restricting layer") as the outermost layer in its electrode. FIG. 9 shows an enzyme electrode having such a structure where an electrode 2 as a working electrode is formed on an insulating substrate 1, on which there are sequentially formed a binding layer 3, an immobilized enzyme layer 4 immobilizing a catalytic enzyme in an organic polymer and a permeation restricting layer 5. Such a permeation restricting layer may restrict an excessive diffusion of the target compound to make an upper limit in determination higher to some extent. In addition, it can prevent the immobilized enzyme layer from being in direct contact with a sample such as urine and blood which may cause deterioration in performance due to protein adhesion or decomposition of the enzyme. A permeation restricting layer has been made of, for example, polyalkylsiloxane (JP-A 10-26601) or silicone (JP-A 6-242068).

JP-A 59-22620 has disclosed a biosensor comprising a permeation restricting layer having a different structure from the above in which a porous TEFLON® (tetrafluoroethylene) or polyfluorovinylidene film as a permeation restricting layer is placed, covering an electrode.

U.S. Pat. No. 5,696,314 has disclosed an enzyme electrode in which a porous permeation restricting layer including TEFLON particles is formed on an immobilized enzyme layer. In the enzyme electrode, as shown in FIG. 11, an electrode 31 made of, for example, platinum and then an immobilized enzyme layer 32 are formed on a substrate 30. Then, a polymer layer 34 comprising the same enzyme as that in the immobilized enzyme layer 32 is formed via an adhesion layer 33, on which there are sequentially formed a permeation restricting layer 35, an adhesion layer 36 and a protection layer 37.

The U.S. patent has disclosed a porous permeation restricting layer 35 essentially comprising polymer particles, metal particles and polymer binder where the polymer particles and the polymer binder are made of TEFLON. The permeation-restriction layer 35 is formed by screen printing. Specifically, TEFLON binder is dissolved in a fluorine-containing solvent, particles such as alumina and TEFLON particles are added, and then the mixture is roll-milled into an ink. The prepared ink is stenciled to form the permeation restricting layer 35.

The above prior art, however, has the following problems.

There will be described problems in the case of using polyalkylsiloxane or silicone as a permeation restricting layer material. Such a material may cause a problem of insufficient durability for long-term use, which is due to inadequate strength of the permeation restricting layer. An enzyme electrode has a structure of plies made of organic materials such as an immobilized enzyme film which may be swollen in a solution. Therefore, the permeation restricting layer with inadequate strength may be intolerant to such film swelling, resulting in, for example, cracks. Thus, long-term use may cause failure of the enzyme electrode.

When determination is repeated with a sample containing a higher level of contaminant for a long time, a sensor output may be remarkably reduced. It may be caused by deterioration of the original permeation restricting property due to adhesion of the contaminant to the permeation restricting layer. In particular, a body fluid may remarkably deteriorate the permeation restricting property because various materials such as urea compounds in addition to proteins are adhered to the permeation restricting layer.

Furthermore, response may become slower when extending a concentration range to be measured to a higher level because when a sample containing a higher level of target compound is analyzed using a conventional permeation restricting layer, it is inevitable to increase the film thickness due to its limitation in selective permeability, leading to a longer time for stabilizing a diffusion rate within the permeation restricting layer.

A technique using a TEFLON or polyfluorovinylidene (JP-A 59-22620) has the following problem.

A technique using a filter comprising, for example, TEFLON has been conventionally used, where the filter is usually disposed outside of an enzyme electrode, covering the electrode because the fluorine compound is, as apparent from its molecular structure, less adhesive to other organic polymer layers such as an immobilized enzyme layer and thus the filter cannot be formed together with the layers including the immobilized enzyme layer. JP-A 59-22620 has disclosed only a configuration where a film consisting of the above fluorine compound is formed on the tip of the enzyme electrode, but not a configuration where the film is adhesively formed in the electrode surface.

Thus, the above prior art has problems that there is formed a certain gap between the permeation restricting layer and the electrode surface, resulting that 1) response becomes slower due to a longer time for a target compound to reach the electrode surface and 2) it takes a longer time for washing, which leads to a longer waiting time for the next determination.

A permeation restricting layer comprising the above fluorine compound must have pores with a diameter of 10 to 100 $\mu$m and be thick adequately to be permeation-restrictive. Thus, response becomes slower and it takes a longer time for washing, leading to a longer waiting time for the next determination.

Furthermore, a permeation restricting layer comprising the above fluorine compound is less flexible. Therefore, the structure is readily broken when a layer disposed nearer to the electrode than the permeation restricting layer is swollen. In particular, the problem is significant when the permeation restricting layer is adjacent to an expansive immobilized enzyme layer.

On the other hand, U.S. Pat. No. 5,696,314 has disclosed a configuration where a permeation restricting layer comprising TEFLON particles and TEFLON binder is formed on an electrode as one part.

As described above, a permeation restricting layer of a polymer with a higher fluorine content such as TEFLON is less adhesive to an adjacent polymer layer such as an immobilized enzyme layer. Therefore, even when the permeation restricting layer is formed with, for example, an immobilized enzyme layer as one part, adhesive strength is insufficient in an interface between these layers. Furthermore, since a permeation restricting layer comprising TEFLON is less flexible, it cannot follow a swollen adjacent layer. Thus, there may readily occur detachment between the permeation restricting layer and its adjacent layer such as an immobilized enzyme layer during operation. Once detachment occurs, there is formed a certain gap between the permeation restricting layer and the electrode surface, resulting that 1) response becomes slower due to a longer time for a target compound to reach the electrode surface and 2) it takes a longer time for washing, which leads to a longer waiting time for the next determination.

When using TEFLON as described in the above publication, it is difficult to prepare a solution due to its less solubility to a solvent. It is, therefore, difficult to deposit a layer by a general process such as spin coating and thus to make the permeation restricting layer thinner. Furthermore, a permeation restricting layer comprising the above fluorine compound must be porous for its permeation restricting property, and therefore, must be thick to some extent. According to the U.S. patent, the thickness is preferably 10 to 40 μm. Thus, it is inevitable to make the permeation restricting layer thick, leading to slower response and a longer washing time.

In addition, a permeation restricting layer comprising TEFLON is less flexible as described above, and therefore tends to be broken when an adjacent layer is swollen. The problem should be also improved. The problem is particularly significant when the permeation-restriction layer is adjacent to an expansive immobilized enzyme layer.

Another technique of the prior art using a fluorine compound will be described, which is not related to an application as a component for a permeation restricting layer.

A fluorine-compound film (TEFLON film) 10 to 50 μm of thickness has been commonly used as an oxygen permeable film and described in, for example, JP-A 56-73342. The film is, however, generally disposed between an immobilized enzyme layer and an electrode, but not on the immobilized enzyme layer. It, therefore, does not act as a permeation restricting layer.

It is also well-known that a NAFION® film, an ion-exchange film, is disposed on an immobilized enzyme layer, which has been disclosed in, for example, JP-A 8-50112. NAFION is a cation-exchange polymer in which perfluoroalkylene ether side chains having a terminal sulfonic group are attached to a perfluoromethylene principal chain (Formula 1).

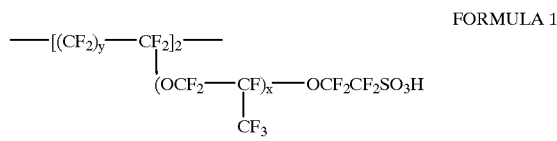

FORMULA 1

A NAFION film disposed on the immobilized enzyme layer may minimize back-diffusion of hydrogen peroxide, reduce variation with time of response to glucose after reaching a peak value and improve response properties. The film is, however, not adequately effective as a permeation restricting layer due to its terminal sulfonic groups. An ion-exchange film is used for preventing permeation of ionic interferent materials interfering an electrode reaction, but little restricts permeation of, for example, excessive glucose.

For a biosensor, it is important to eliminate effects of interferent materials or contaminants. An interferent material refers to a chemical substance which may affect the above oxidation-reduction reaction system to give a positive error in a measurement result, such as ascorbic acid and acetaminophen. A contaminant refers to a chemical substance which may be adsorbed by an electrode surface to give a negative error in a measurement result. For example, Bioindustry, Vol.9, No.12, pp.20–25 (1992) has list albumin, urea, urea compounds and creatinine as a contaminant to a sensor output, i.e., a substance giving a negative error.

JP-A 8-180286 has disclosed a biosensor in which a permeation restricting layer of polyalkylsiloxane and NAFION or acetylcellulose is deposited as an enzyme electrode for eliminating effects of a higher level of interferent materials on a sensor output. FIG. 26 shows its configuration where an electrode 12 is formed on an insulating substrate 11, on which there are sequentially formed a y-aminopropyl-triethoxysilane film 13, an acetylcellulose film 14, a perfluorocarbonsulfonic acid film 15, an immobilized enzyme layer 16 and a polyalkylsiloxane film 17. The publication describes that such a layered structure may prevent a higher level of interferent materials from reaching an electrode surface.

JP-A 3-72254 has disclosed a biosensor in which a permeation restricting layer of NAFION and polyurethane is deposited as an enzyme electrode for eliminating effects of interferent materials or contaminants on a sensor output. FIG. 27 shows its configuration where a working electrode 23, a control electrode 24 and an insulative protection film 25 are formed on a plastic film 22 and an immobilized enzyme layer 29 is formed covering these films. The immobilized enzyme layer 29 consists of a NAFION film 29a, an enzyme layer 29b and a polyurethane layer 29c. The publication describes that such a structure of electrode may reduce permeation or adhesion of an interferent or concomitant material to an electrode.

It has been difficult to eliminate a contaminant such as urea compounds during measurement for a body fluid such as urine or blood containing the contaminant at a higher level when such an enzyme electrode is used. For example, an acetylcellulose film can restrict permeation of a higher molecular-weight compound, but not adequately restrict permeation of a lower molecular-weight compound such as urea.

Therefore, a contaminant such as urea compounds may reach an electrode surface to be irreversibly adsorbed. Thus, repeated use may cause reduction in a sensor output with time, and resultantly such a sensor is less reproductive for repeated measurement or less stable for a long-term use. Furthermore, an urea compound, once adsorbed by an electrode, cannot be easily removed by washing with water. It may lead to a longer waiting time for the next measurement and particularly for repeated measurement, an accumulated negative error may be more significant depending on the measurement number.

Such a problem of adsorption of a contaminant such as an urea compound is significant particularly when platinum is used as an electrode material because an urea compound tends to adhere to platinum. However, an electrode is generally made of platinum having good chemical resistance and good detection properties for hydrogen peroxide. Thus, it has been strongly desired to develop an enzyme electrode which may solve the above problems.

SUMMARY OF THE INVENTION

In the light of the above problems, an objective of this invention is to provide an enzyme electrode allowing highly sensitive and stable measurement even in a long-term use as well as a biosensor and a measuring apparatus therewith.

For achieving the objective, this invention provides an enzyme electrode which can perform detection under a wide range of working conditions and has a good durability for a long-term use, by forming a permeation restricting layer with a particular structure of polymer.

Furthermore, this invention can eliminate effects of contaminants or interferent materials on a measured value in determination for a body fluid sample such as urine, blood and sweat containing urea compounds at a higher level and prevent reduction of a sensor output for a consistently reproductive output, by forming an electrode protection layer comprising an urea compound.

This invention will be described in detail.

This invention provides an enzyme electrode comprising an electrode on an insulating substrate, an immobilized enzyme layer on the electrode and a permeation restricting layer on the immobilized enzyme layer, said permeation restricting layer mainly consisting of a polymer in which a pendant group containing at least a fluoroalkylene block is attached to a non-fluorinated vinyl polymer.

The enzyme electrode consists of an electrode (electrode layer) on an insulating substrate and multiple layers having different functions on the electrode. The permeation restricting layer is made of a polymer having a pendant group comprising a fluoroalkylene block (fluoroalkylene unit). Such a configuration may prevent adhesion of contaminants such as proteins and urea compounds to provide an enzyme electrode exhibiting stable output properties even for a long-term use. The fluoroalkylene moiety may not contribute to dissolution into a washing agent such as non-fluorinated solvent and a surfactant, providing an enzyme electrode with good chemical resistance.

The polymer has a non-fluorinated vinyl polymer structure as a principal chain, which is highly adhesive to another organic polymer layer such as an immobilized enzyme layer. It, therefore, does not cause a gap between a layer such as the immobilized enzyme layer on the electrode surface and the permeation restricting layer. It may allow response to be faster and a time for washing to be reduced. In addition, its good adhesiveness may improve durability of the layered structure to provide an enzyme electrode resistant to deterioration due to a long-term use. The polymer may have, in addition to the pendant group comprising a fluoroalkylene block, any other appropriate side chain or functional group; for example, a properly polar functional group such as —OH and —COOH groups may further improve adhesiveness to another organic polymer layer such as an adjacent immobilized enzyme layer.

The polymer composing the permeation restricting layer has a unique structure that a pendant group comprising at least a fluoroalkylene block is attached to a non-fluorinated vinyl polymer chain, exhibiting a good permeation restricting property when used in, for example, a glucose sensor. Thus, it may significantly extend a measurable concentration range. Furthermore, its excellent permeation restricting property may allow the permeation restricting layer to be thinner, for example, below 0.1 $\mu$m, leading to faster response and a reduced time for washing.

The permeation restricting layer may be formed as a homogeneous film by a convenient process such as dip-coating, spin-coating and spray-coating and may be suitable for mass production.

This invention also provides an enzyme electrode comprising an electrode on an insulating substrate, an immobilized enzyme layer on the electrode and a permeation restricting layer on the immobilized enzyme layer, said permeation restricting layer consisting of a polycarboxylic acid (A) fluoroalcohol ester.

This invention also provides an enzyme electrode comprising an electrode on an insulating substrate, an immobilized enzyme layer on the electrode and a permeation restricting layer on the immobilized enzyme layer, said permeation restricting layer comprising a polycarboxylic acid (A) fluoroalcohol ester and a polycarboxylic acid (B) alkylalcohol ester.

This invention also provides an enzyme electrode comprising an electrode on an insulating substrate, an immobilized enzyme layer on the electrode and a permeation restricting layer on the immobilized enzyme layer, said permeation restricting layer mainly consisting of a polycarboxylate comprising alkylalcohol ester and fluoroalcohol ester groups.

These enzyme electrodes consist of an electrode (electrode layer) on an insulating substrate and multiple layers having different functions on the electrode, characterized in that the permeation restricting layer is composed of a polymer having a particular structure.

An enzyme electrode according to this invention is made of a fluoroalcohol polycarboxylate. A fluoroalcohol polycarboxylate refers to a polycarboxylic acid, whose carboxyl groups are partially or totally esterified with a fluoroalcohol. A fluoroalcohol refers to an alcohol, at least one or all of whose hydrogen atoms are replaced with fluorine atom(s).

The permeation restricting layer material has a fluoroalcohol ester group, which may prevent adhesion of contaminants such as proteins and urea compounds, leading to an enzyme electrode exhibiting a stable output property when used for a long term.

The permeation restricting layer material having a fluoroalcohol ester group may prevent adhesion of contaminants such as proteins and urea compounds, leading to an enzyme electrode exhibiting a stable output property for a long-term use. The fluoroalcohol ester group may not contribute to dissolution into a washing agent such as almost all kinds of non-fluorinated solvents and surfactants, providing an enzyme electrode with good chemical resistance.

These enzyme electrodes have a permeation restricting layer comprising a polymer having a principal chain of a polycarboxylic acid, to which a fluoroalcohol is attached via an ester group. The polymer is highly adhesive to another organic polymer layer such as an immobilized enzyme layer. It, therefore, does not cause a gap between a layer such as the immobilized enzyme layer on the electrode surface and the permeation restricting layer. It may allow response to be faster and a time for washing to be reduced. In addition, its good adhesiveness may improve durability of the layered structure to provide an enzyme electrode resistant to deterioration due to a long-term use. The polymer may have, in addition to the fluoroalcohol ester group, any other appropriate functional group to the principal chain; a properly polar functional group may further improve adhesiveness to another organic polymer layer such as an adjacent immobilized enzyme layer.

The polymer composing the permeation restricting layer has a unique structure that the carboxyl groups of the polycarboxylic acid are partially or totally esterified with a fluoroalcohol, which may significantly extend a measurable concentration range when used in, for example, a glucose sensor. Furthermore, its excellent permeation restricting property may allow the permeation restricting layer to be thinner, for example, below 0.1 µm, leading to faster response and a reduced time for washing.

The permeation restricting layer may be formed as a homogeneous film by a convenient process such as dipcoating, spin-coating and spray-coating and may be suitable for mass production.

When a permeation restricting layer comprises (a) a polycarboxylic acid (A) fluoroalcohol ester and a polycarboxylic acid (B) alklylalcohol ester or (b) a polycarboxylate having an alkylalcohol ester and a fluoroalcohol ester groups, high temperature stability may be improved, in addition to the above effects. An enzyme electrode or a biosensor therewith may be sometimes stored or used at a relatively higher temperature (for example, ca. 40° C.). When used for measurement after leaving at a higher temperature, sensitivity of a conventional enzyme electrode has often varied significantly, compared to measurement before exposure to the higher temperature. On the other hand, an enzyme electrode or biosensor comprising the above permeation restricting layer little varies in its sensitivity even after exposure to a higher temperature.

In an enzyme electrode of this invention as described above, an electrode and an immobilized enzyme layer may be formed in direct contact with each other or another layer may intervene these layers. For example, a binding layer mainly consisting of a silane coupling agent is disposed between the electrode and the immobilized enzyme layer or an ion-exchange polymer layer mainly consisting of an ion-exchange polymer having a perfluorocarbon skeleton is disposed between the binding layer and the immobilized enzyme layer. Similarly, the immobilized enzyme layer and the permeation restricting layer may be formed in direct contact with each other or another layer may intervene these layers.

This invention also provides a method for manufacturing an enzyme electrode comprising the steps of: forming an electrode on an insulating substrate, applying the first liquid containing an enzyme to the electrode directly or via another layer and then drying it to form an immobilized enzyme layer, and applying the second liquid containing a polymer in which a pendant group having at least a fluoroalkylene block is attached to a non-fluorinated vinyl polymer, to the immobilized enzyme layer directly or via another layer and then drying it to form a permeation restricting layer.

In this manufacturing process, a permeation restricting layer is formed by applying and then drying the second liquid comprising a polymer having the above particular structure. Thus, there may be provided, with a good controllability for a film thickness, a permeation restricting layer which is excellent in stability for repeated measurement, adhesiveness to adjacent layers, durability and permeation restricting property. Since the second liquid has a lower viscosity, the permeation restricting layer may be readily formed with a reduced film thickness. Specifically, a permeation restricting layer 0.01 to 3 µm of thickness after drying may be satisfactorily formed.

This invention also provides a biosensor using the above enzyme electrode as a working electrode. The biosensor has a permeation restricting layer comprising the polymer having the above particular structure on the enzyme electrode surface. It, therefore, may be excellent in long-term stability and may be used under a wide range of measuring conditions.

Although the above description is related to an enzyme electrode and other entities comprising a permeation restricting layer composed of a polymer having a particular structure, this invention also provides an enzyme electrode and other entities comprising an electrode protection layer having a particular structure.

This invention also provides an enzyme electrode comprising an electrode on an insulating substrate, an electrode protection layer comprising an urea compound covering at least a part of the electrode, and an immobilized enzyme layer covering the electrode and the electrode protection layer.

The enzyme electrode consists of an electrode (electrode layer) on an insulating substrate and multiple layers having different functions on the electrode, which may be used as a detection element in a biosensor, in particular a biosensor for determining, for example, glucose in a sample such as urine, blood and sweat.

In this enzyme electrode, an electrode protection layer containing an urea compound is formed on an electrode surface on an insulating layer. An urea compound is, as described above, a contaminant which may give a negative error to a measurement result when adhering to the electrode surface. The enzyme electrode of this invention has an electrode protection layer comprising such a contaminant on the electrode surface in advance, for preventing contaminants in a sample from reaching the electrode surface during measurement and thus minimizing variation in sensitivity.

An electrode protection layer comprising an urea compound may degrade absolute sensitivity, but the degree may be practically insignificant. On the other hand, sensitivity variation with time associated with repeated operation may be remarkably improved in comparison with a conventional type of enzyme electrode which does not have an electrode protection layer.

Furthermore, an electrode protection layer may restrict permeation of interferent materials such as ascorbic acid and acetaminophen. Compared with permeation of these interferent materials, the layer may be less restrictive to permeation of hydrogen peroxide. Thus, the layer may improve selective permeability for hydrogen peroxide.

The enzyme electrode of this invention has an electrode protection layer functioning as described above. Thus, a sensor output reduction with time due to an urea compound and a sensor output increase due to interferent materials are prevented for a stable output. Furthermore, it may provide a more sensitive sensor than that according to the prior art.

This invention also provides a method for manufacturing an enzyme electrode comprising the steps of: forming an electrode on an insulating substrate surface, and then applying electricity to the insulating substrate while being soaked in a mixed solution comprising a supporting electrolyte and an urea compound to cover at least a part of the electrode with an electrode protection layer comprising the urea compound.

The process for manufacturing an enzyme electrode employs electrolysis for selectively forming urea-compound layers on individual electrodes. Forming an urea-compound layer and patterning may be simultaneously conducted, which may simplify the manufacturing process and readily lead to mass production. Furthermore, the urea-compound layer may be formed, independently of the size or shape of the electrode.

This invention also provides a biosensor using the above enzyme electrode as a working electrode. The biosensor has an enzyme electrode having an electrode protection layer comprising an urea compound which covers at least a part of the electrode. It, therefore, may prevent sensor output reduction with time due to urea compounds and sensor output increase due to interferent materials for giving a stable output. Furthermore, it may realize higher sensitivity than that of the prior art. A biosensor according to this invention may have further have a counter electrode and a reference electrode on an insulating substrate. It is preferable that the enzyme electrode (working electrode) and the counter electrode are made of platinum while the reference electrode is made of silver/silver chloride because urea is easily attached to platinum so that an electrode protection layer comprising an urea compound may be suitably formed on the enzyme electrode (working electrode) or the counter electrode.

This invention also relates to a variety of measuring apparatus using the above biosensor. Specifically, this invention provides a measuring apparatus comprising the above biosensor and a data indicator indicating an electric signal from the biosensor.

This invention also provides a measuring apparatus comprising the above biosensor, an electrochemical measuring circuit receiving an electric signal from the biosensor, a data processor calculating a measured value based on the electric signal and a data indicator indicating the measured value.

These measuring apparatus may realize highly sensitive and stable measurement because of their biosensor having a particular structure of working electrode. They are also easily operated even by an unfamiliar individual.

As described above, an enzyme electrode of this invention comprising a permeation restricting layer mainly consisting of a particular structure of polymer or a biosensor therewith has the following advantages.

First, it may prevent adhesion of contaminants such as proteins and urea compounds to realize a stable output property for a long-term use because a pendant group containing a fluoroalkylene block such as a fluoroalcohol ester group contributes to insolubility in a washing agent such as almost all non-fluorinated solvents and surfactants. It, therefore, may give stable repeated measuring results even for a test system comprising a variety of chemical compounds such as a body fluid.

Secondly, the permeation restricting layer has good adhesiveness to another organic polymer layer such as an immobilized enzyme layer, leading to faster response, a reduced time for washing and improved durability of the layered structure, to provide an enzyme electrode unsusceptible to damage due to a long-term use. Such good adhesiveness may be endowed because the polymer has a principal chain consisting of a non-fluorinated vinyl polymer. A structure in which a pendant group is attached to a principal chain via an ester group may further improve adhesiveness.

Thirdly, it may provide a good permeation-restricting property to significantly extend a measurable concentration range. Such a good permeation-restricting property may be endowed because the polymer composing of the permeation restricting layer has a particular structure in which a pendant group containing at least a fluoroalkylene block is attached to a non-fluorinated vinyl polymer chain.

Fourthly, a good permeation-restricting property may allow the permeation restricting layer to be thinner for achieving faster response and a reduced time for washing.

Fifthly, it may allow stable measurement for an ionized substance such as lactic acid because the permeation restricting layer has no charges and therefore little interacts with an ionic substance.

An enzyme electrode of this invention comprising an electrode protection layer containing an urea compound and a biosensor therewith may be used to precisely determine a particular ingredient in a sample containing a higher level of contaminants such as urea because the electrode protection layer prevents the contaminants such as urea in the sample from permeating to the electrode. The electrode protection layer can prevent permeation of interferent materials such as ascorbic acid and acetaminophen, to improve selective permeation of a target substance such as hydrogen peroxide. Thus, the enzyme electrode or the biosensor of this invention may prevent sensor output reduction with time due to urea compounds and sensor output increase due to interferent materials for a stable output. Furthermore, such improvement in selectivity may realize a higher sensitive sensor than that of the prior art.

An electrode protection layer containing an urea compound may be formed by electrolysis. Thus, urea- compound layers may be selectively formed on individual electrodes. Therefore, forming an urea-compound layer and patterning may be simultaneously conducted, which may simplify the manufacturing process and readily lead to mass production. Furthermore, the urea-compound layer may be formed, independently of the size or shape of the electrode.

DETAILED DESCRIPTION OF THE PREFERRED EMBODIMENTS

Figure 1:
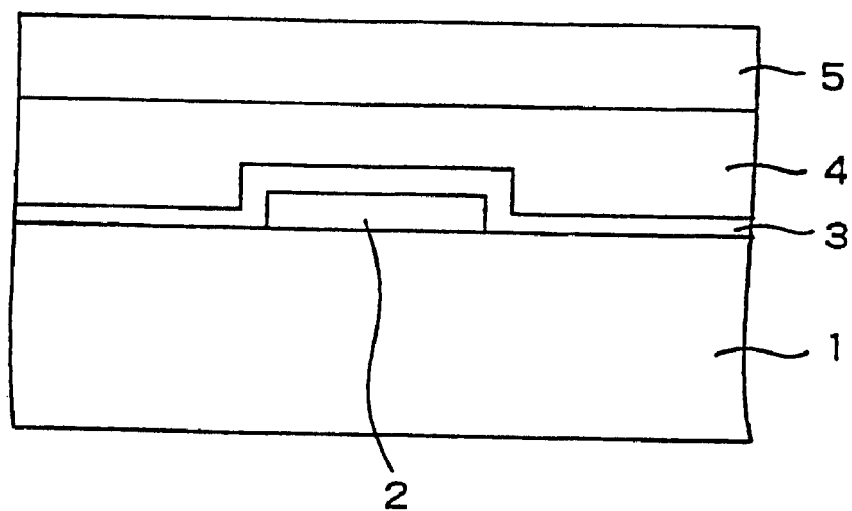
FIG. 1 is a cross section of an embodiment of an enzyme electrode according to this invention.

As used herein, an "enzyme electrode" refers to an electrode comprising an immobilized enzyme layer. A "biosensor" refers to a device element comprising the enzyme electrode and, as necessary, a counter electrode and/or a reference electrode. As used herein, a "measuring apparatus" refers to a system comprising the above biosensor and equipped with a variety of means for indicating and processing an electric signal from the biosensor. An enzyme electrode, a biosensor and a measuring apparatus according to this invention will be described in detail.

The first enzyme electrode according to this invention comprises an electrode on an insulating substrate, an immobilized enzyme layer on the electrode and a permeation restricting layer on the immobilized enzyme layer where the permeation restricting layer mainly consists of a polymer in which a pendant group containing at least a fluoroalkylene block is attached to a non-fluorinated vinyl polymer.

The term "mainly consist(ing) of" means that the above polymer is a main component composing of the permeation restricting layer; for example, the polymer is contained in a proportion of 50 wt % or higher in the permeation restricting layer.

A "non-fluorinated vinyl polymer" is a moiety for improving adhesiveness to another organic polymer layer such as an immobilized enzyme layer. There are, therefore, no limitations in terms of its structure, but it must have no fluorine atoms. If a polymer part other than a pendant group contains a fluorine atom, a permeation restricting layer may be less adhesive to another organic polymer layer such as an immobilized enzyme layer, making it difficult to prepare a solution or to form a permeation restricting layer as a thin film.

A non-fluorinated vinyl polymer is a polymer having a principal chain composed of carbon-carbon chain; preferably a homopolymer or copolymer of one or more monomers selected from the group consisting of unsaturated hydrocarbons, unsaturated carboxylic acids and unsaturated alcohols; most preferably a polycarboxylic acid. An appropriate polymer may be selected for improving adhesiveness to another organic polymer layer such as an immobilized enzyme layer to provide a permeation restricting layer having good durability. It is preferable that a fluoroalkylene block is attached to a vinyl polymer via an ester group, which is appropriately polar to further improve adhesiveness to another organic polymer layer such as an immobilized enzyme layer. Such polymers include 1H,1H-perfluorooctyl polymethacrylate and 1H,1H,2H,2H-perfluorodecyl polyacrylate.

A pendant group containing a fluoroalkylene block is one having a fluoroalkylene group as a unit. A fluoroalkylene group means an alkylene group whose hydrogens are partially or totally replaced with fluorines. A fluorine content in the pendant group, i.e., a value of $x/(x+y)$ where x and y are the numbers of fluorine and hydrogen atoms in the pendant group, respectively, is preferably 0.3 to 1, more preferably 0.8 to 1, which may prevent adhesion of contaminants to the permeation restricting layer and give good permeation-restricting property.

The pendant group preferably has 3 to 15 carbon atoms, more preferably 5 to 10 carbon atoms, most preferably 8 to 10 carbon atoms, to make the length of the pendant group appropriate for providing good film-deposition property and permeation-restricting property and maintaining good adhesiveness to an adjacent polymer layer.

The binding rate of the pendant group to the vinyl polymer, i.e., the content of the pendant group, is not particularly limited, but may be appropriately determined depending on the other polymers and its application; for example, 0.1 to 30%. The content of the water-repellent pendant group may be thus selected in an appropriate range to realize good permeation-restriction property and good adhesiveness to an adjacent polymer layer. The binding rate of the pendant group means the proportion of the pendant group to all the groups attached to the carbon—carbon chain as the principal chain of the vinyl polymer. For example, where a vinyl polymer as a principal chain is polyacrylate, 10% of whose —COOH groups are esterified to be a pendant group, the binding rate of the pendant group is 2.5% obtained by multiplying the binding rate of —COOH group, 25%, by the esterification rate, 10%.

The polymer composing of the permeation restricting layer may be preferably 1000 to 50000, more preferably 3000 to 20000. If it is too high, it is difficult to prepare a solution, while if it is too low, adequate permeation-restricting property is not provided. A molecular weight herein is a number average molecular weight.

The second enzyme electrode according to this invention comprises an electrode on an insulating substrate, an immobilized enzyme layer on the electrode and a permeation restricting layer on the immobilized enzyme layer where the permeation restricting layer mainly consists of a polycarboxylic acid (A) fluoroalcohol ester. The term "mainly consist(ing) of" means that the above polymer is a main component composing of the permeation restricting layer; for example, the polymer is contained in a proportion of 50 wt % or higher in the permeation restricting layer.

The third enzyme electrode according to this invention comprises an electrode on an insulating substrate, an immobilized enzyme layer on the electrode and a permeation restricting layer on the immobilized enzyme layer where the permeation restricting layer comprises a polycarboxylic acid (A) fluoroalcohol ester and a polycarboxylic acid (B) alkylalcohol ester.

The fourth enzyme electrode according to this invention comprises an electrode on an insulating substrate, an immobilized enzyme layer on the electrode and a permeation restricting layer on the immobilized enzyme layer where the permeation restricting layer mainly consists of a polycarboxylate having an alkylalcohol ester and a fluoroalcohol ester groups. The term "mainly consist(ing) of" means that the above polymer is a main component composing of the permeation restricting layer; for example, the polymer is contained in a proportion of 50 wt % or higher in the permeation restricting layer.

Examples of the polycarboxylic acid composing of the polycarboxylic acid (A) or (B) or the above polycarboxylate include polymers having a carboxylic acid unit such as acrylic acid, methacrylic acid, fumaric acid and itaconic acid; specifically polymethacrylic acid, polyacrylic acid and a copolymer of acrylic acid and methacrylic acid. The polycarboxylic acids (A) and (B) may be the same or different.

A fluorine content in the fluroalcohol ester group, i.e., a value of x/(x+y) where x and y are the numbers of fluorine and hydrogen atoms in the fluoroalcohol ester group, respectively, is preferably 0.3 to 1, more preferably 0.8 to 1, which may prevent adhesion of contaminants to the permeation restricting layer and give good permeation-restricting property.

The fluoroalcohol moiety composing of the fluoroalcohol ester group preferably has 3 to 15 carbon atoms, more preferably 5 to 10 carbon atoms, most preferably 8 to 10 carbon atoms, to make the length of the fluoroalcohol ester group appropriate for providing good film-deposition property and permeation-restricting property and maintaining good adhesiveness to an adjacent polymer layer.

The esterification rate of the polycarboxylic acid fluoroalcohol ester is not particularly limited, but may be appropriately determined depending on the other polymers and its application; for example, 0.1 to 30%. The esterification rate means the rate of the esterified carboxylic acid groups belonging to the polyacrylic acid moiety in the principal chain. The esterification rate may be selected within the above range to make the content of the water-repelling fluoroalcohol ester group proper for realizing good permeation-restriction property and good adhesiveness to an adjacent polymer layer.

In this invention, the fluoroalcohol composing of the fluoroalcohol ester is preferably a primary alcohol because it may effectively prevent adhesion of contaminants to the permeation restricting layer and may provide excellent chemical resistance to acids, alkalis or a variety of organic solvents. Preferable examples of the alcohol include 1H,1H-perfluorooctyl polymethacrylate and 1H,1H,2H,2H-perfluorodecyl polyacrylate.

The permeation restricting layer may comprise a polycarboxylic acid (A) fluoroalcohol ester and a polycarboxylic acid (B) alkylalcohol ester or may mainly consist of a polycarboxylate comprising an alkylalcohol ester and a fluoroalcohol ester groups, to provide an enzyme electrode exhibiting improved high-temperature stability.

A preferable type of "fluoroalcohol ester" is as described above.

The alkylalcohol moiety in the alkylalcohol ester part means a straight or circular alcohol represented by $C_nH_{n+2}OH$ (n is a natural number) where n is an integer of 1 or more, preferably 2 to 10, more preferably 4 to 8, most preferably 6. For example, hexyl and cyclohexyl groups may be suitable. Thus, stability of the enzyme electrode may be further improved when exposed to an elevated temperature.

When the permeation restricting layer comprises a polycarboxylic acid (A) fluoroalcohol ester and a polycarboxylic acid (B) alkylalcohol ester, the content of the polylcarboxylic acid (A) fluoroalcohol ester to the overall permeation restricting layer is preferably 50 to 99 wt %, more preferably 75 to 99 wt %, most preferably 80 to 95 wt %. If the content is too low, the permeation restricting layer may be less durable while if the content is too high, the permeation restricting layer may exhibit insufficient stability when exposed to an elevated temperature. On the other hand, the content of the polylcarboxylic acid (B) alkylalcohol ester to the overall permeation restricting layer is preferably 1 to 50 wt %, more preferably 1 to 25 wt %, most preferably 5 to 20 wt %. If the content is too low, the permeation restricting layer may exhibit insufficient stability when exposed to an elevated temperature, while if the content is too high, the permeation restricting layer may be less durable. A polycarboxylic acid (B) alkylalcohol ester means a polycarboxylic acid (B) which is at least partially esterified with the above alkylalcohol; preferably cyclohexyl polymethacrylate.

When the permeation restricting layer comprises a polycarboxylate comprising an alkylalcohol ester and a fluoroalcohol ester groups, preferable types of individual ester groups are as described above and a variety of combination of these ester groups may be employed. The ratio between the alkylalcohol ester and the fluoroalcohol ester groups is not particularly limited, but a/b where "a" and "b" are the numbers of the fluoroalcohol ester group and of the alkylalcohol ester group, respectively, is preferably 50/50 to 99/1, more preferably 75/25 to 99/1, most preferably 80/20 to 95/5.

Preferable polycarboxylates include those containing a cyclohexyl polymethacrylate unit; for example those containing the repeating unit represented formula (2), which may improve high-temperature stability and permeation-restricting property.

FORMULA 2

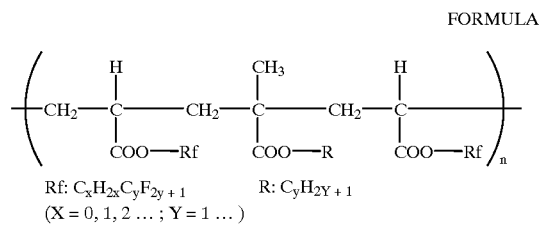

Rf: $C_xH_{2x}C_yF_{2y+1}$  R: $C_yH_{2Y+1}$
(X = 0, 1, 2 ... ; Y = 1 ... )

where n is an integer of 2 or more, X is an integer of 0 or more, and Y is an integer of 1 or more.

Specific compounds include a copolymer of 1H,1H-perfluorooctyl methacrylate and cyclohexyl methacrylate and a copolymer of 1H,1H,2H,2H-perfluorodecyl acrylate and cyclohexyl methacrylate; preferably a compound represented by formula (3) having the repeating units of 1H,1H,2H,2H-perfluorodecyl acrylate and of cyclohexyl methacrylate.

FORMULA 3

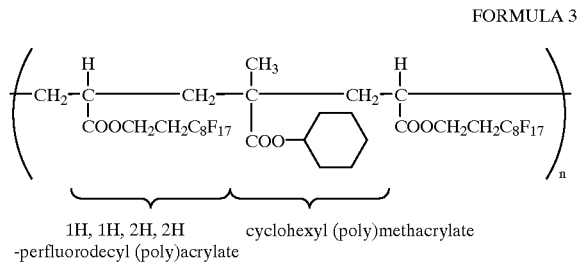

1H, 1H, 2H, 2H -perfluorodecyl (poly)acrylate   cyclohexyl (poly)methacrylate where n is an integer of 2 or more.

These copolymers may be used to improve particularly high-temperature stability and other properties such as permeation-restricting property.

A permeat ion restricting layer in an enzyme electrode according to this invention comprises a particular structure of polymer, but may comprises a mixture of two or more polymers whose structures and/or molecular weights are different from each other.

For the above first to fourth enzyme electrodes, the molecular weight of a polylcarboxylic acid (A) fluoroalcohol ester or a polycarboxylate containing an alkylalcohol ester and a fluoroalcohol ester groups composing of the permeation restricting layer is preferably 1000 to 50000, more preferably 3000 to 30000. If it is too high, it is difficult to prepare a solution, while if it is too low, adequate permeation-restricting property is not provided. A molecular weight herein is a number average molecular weight.

In these enzyme electrodes, the thickness of the permeation restricting layer is preferably 0.01 to 3 μm, more preferably 0.01 to 1 μm, most preferably 0.01 to 0.1 μm, which may lead to improvement in response speed and reduction in a washing time.

This invention also provides a method for manufacturing an enzyme electrode comprising the steps of: forming an electrode on an insulating substrate, applying the first liquid containing an enzyme to the electrode directly or via another layer and then drying it to form an immobilized enzyme layer, and applying the second liquid containing a polymer in which a pendant group having at least a fluoroalkylene block is attached to a non-fluorinated vinyl polymer, to the immobilized enzyme layer directly or via another layer and then drying it to form a permeation restricting layer. Preferably embodiments of "a polymer in which a pendant group having at least a fluoroalkylene block is attached to a non-fluorinated vinyl polymer" or others are as described for the first to fourth enzyme electrodes according to this invention; for example, polycarboxylic acid fluoroalcohol esters such as 1H,1H-perfluorooctyl polymethacrylate, 1H,1H,2H,2H-perfluorodecyl polyacrylate, a copolymer of 1H,1H-perfluorooctyl methacrylate and cyclohexyl methacrylate, and a copolymer of 1H,1H,2H,2H-perfluorodecyl acrylate and cyclohexyl methacrylate.

The fifth enzyme electrode according to this invention comprises an electrode on an insulating substrate, an electrode protection layer mainly consisting of an urea compound, covering at least a part of the electrode, and an immobilized enzyme layer covering the electrode and the electrode protection layer.

In this enzyme electrode, the electrode protection layer comprises an urea compound. Its content is not particularly limited, but the layer may substantially consist of the urea compound. The term, "mainly consist of" herein means that the content of the urea compound in the electrode protection layer is 50 wt % or higher.

The electrode protection layer is preferably formed, covering the overall surface, but may cover a part of the electrode surface. There are no limitations for the thickness of the electrode protection layer. However, since an electrode protection layer consisting of urea formed by electrolysis may be sufficiently effective as described later in Examples, an average thickness corresponding to a ply of several molecules, for example, about 0.1 to 50 nm, may be adequate.

The electrode protection layer and the immobilized enzyme layer in the enzyme electrode of this invention may be formed to be adjacent to each other directly or via an intervening layer. For example, a binding layer mainly consisting of a silane coupling agent is disposed between the electrode protection layer and the immobilized enzyme layer or an ion-exchange polymer layer mainly consisting of an ion-exchange polymer having a perfluorocarbon skeleton is disposed between the electrode protection layer and the immobilized enzyme layer. In this invention, an electrode on an insulating substrate is an electrode functioning at least as a working electrode.

When a biosensor equipped with the fifth enzyme electrode is used, an urea compound may be added to a preserving solution or a calibration solution, to further improve stability in measurement.

Figure 10:
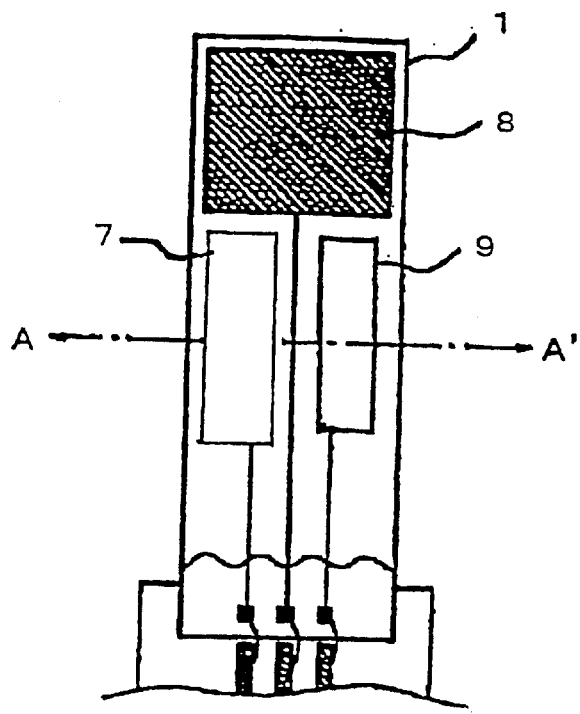
FIG. 10(a) schematically shows a biosensor according to this invention.
FIG. 10(b) shows cross-section A–A' from FIG. 10(a).
Figure 10:
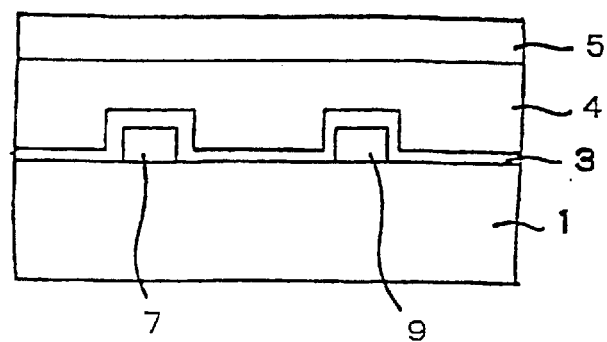
Figure 11:
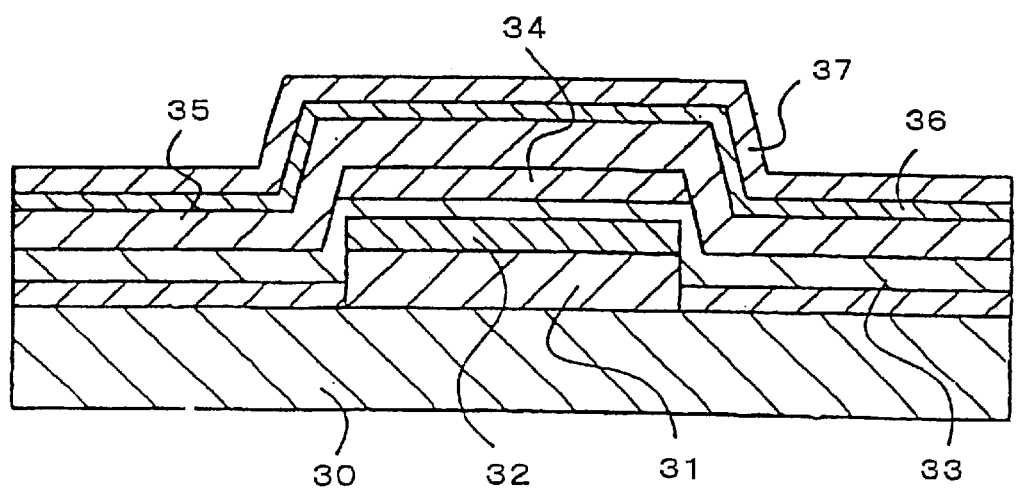
FIG. 11 is a cross section of a conventional enzyme electrode.

FIG. 10 shows an example of a biosensor employing an enzyme electrode of this invention, where the enzyme electrode is used as a working electrode 7 and a counter electrode 8 and a reference electrode 9 are formed on a quartz substrate. The working electrode 7 and the counter electrode 8 are platinum electrodes, and the reference electrode 9 is a silver/silver chloride electrode. On the working electrode are sequentially formed a binding layer 3 mainly consisting of γ-aminopropyltriethoxysilane, an immobilized enzyme layer 4 in which a catalytic enzyme is immobilized in an organic polymer molecule, and a permeation restricting layer 5 consisting of a fluoroalcohol methacrylate resin. The working electrode 7, the counter electrode 8 and the reference electrode 9 are connected to corresponding measuring systems, respectively.

This figure shows an example of an amperometric type of sensor, but the enzyme electrode of this invention may be, of course, applied to an ion-sensitive field effect transistor type of sensor.

A biosensor according to this invention is particularly effective when used as an urinary-sugar sensor determining a glucose (urinary sugar) level in urine.

A lower limit to urinary sugar is 50 mg/dL for a conventional sensor while the sensor of this invention can detect 1 to 5 mg/dL. In a conventional measuring apparatus, an S/N ratio is high so that when attempting to determine a low level of glucose below 50 mg/dL, a sensor output may be hidden by noises, making quantitative determination difficult. On the other hand, in a sensor according to this invention, an S/N ratio is adequately low to perform precise determination even in a low concentration range. Since a healthy individual has an urinary sugar value of 2 to 10 mg/dL, such improvement in measuring sensitivity is quite significant. Using a biosensor according to this invention, an urinary sugar level below 50 mg/dL can be quantitatively determined. An urinary sugar level can be, therefore, determined for an individual whose urinary sugar level is within a normal range or a prediabetic individual to collect data useful in prophylaxis for diabetes.

When using a sensor according to this invention, influence of urea, vitamin C and acetaminophen contained in a large amount in urine may be effectively eliminated. Therefore, precise determination may be performed even after a subject takes a soft drink containing a large amount of vitamin C or an antipyretic containing acetaminophen.

In a measuring apparatus according to this invention, a biosensor is preferably removable because it is desirable that the electrode of the biosensor is readily exchangeable since the electrode is consumable. Only the biosensor may be removable or wirings connecting the biosensor to other parts or a part comprising the biosensor may be removable. For example, in the measuring apparatus shown in FIG. 31, a wiring 54 between a biosensor 50 and an electrochemical measuring circuit 51 may be removable, or a part consisting of the biosensor 50, the wiring 54 and the electrochemical measuring circuit 51 may be removable.

A data processor in a measuring apparatus according to this invention calculates a determination value based on an electric signal from a biosensor; for example, it operates by converting the electric signal to an analogue signal and/or a digital signal for calculating a determination value. The data processor may be equipped with a variety of means; for example, some or all of the following means;

(a) a timer,
(b) a time setting means for setting a time and a time indicator indicating a time at the time set by the time setting means,
(c) an operation guide means describing operation instructions for the measuring apparatus,
(d) a measured-value storing means for storing a calculated measured value,
(e) a password registration means for registering a password for a user of the measuring apparatus,
(f) a memo registration means for registering a memo,
(g) an operation indicator for detecting malfunction in the measuring apparatus,
(h) a calibration-timing indicator for detecting and indicating a calibration timing for the enzyme electrode,
(i) an electrode-replacement-timing indicator for detecting and indicating a replacement timing for the enzyme electrode,
(j) an abnormal-current indicator for detecting and indicating an abnormal current, and
(k) an electrode calibrator for calibrating the enzyme electrode.

Such a configuration may further improve operability. Processed results from one or more of (a) to (k) are indicated by the indicator.

Embodiments of this invention will be further described with reference to the drawings.

Embodiment 1

The first embodiment will be described with reference to FIG. 1. The enzyme electrode of this embodiment comprises an electrode 2 as a working electrode on an insulating substrate 1, on which a binding layer 3 mainly consisting of γ-aminopropyltriethoxysilane is formed. On the binding layer are sequentially formed an immobilized enzyme layer 4 in which a catalytic enzyme is immobilized 4a in an organic polymer and a permeation restricting layer 5 consisting of a fluoroalcohol methacrylate resin.

The insulating substrate 1 may mainly consisting of a highly-insulative material such as ceramics, glass, quartz and plastics, which is preferably excellent in waterproof, heat resistance, chemical resistance and adhesiveness to an electrode.

The electrode 2 may mainly consist of a material such as platinum, gold, silver and carbon; platinum is particularly preferable because of its excellent chemical resistance and detection property for hydrogen peroxide. The electrode 2 on the insulating substrate 1 may be formed by, for example, spattering, ion plating, vacuum deposition, chemical paper deposition and electrolysis; spattering is particularly preferable because the electrode 2 is highly adhesive to the insulating substrate 1 and a platinum layer can be easily formed. Furthermore, a titanium or chromium layer may be inserted between these layers for improving adhesiveness of the insulating substrate 1 to the electrode 2.

The binding layer 3 on the electrode 2 may improve adhesiveness (binding strength) of the immobilized enzyme layer 4 to the insulating substrate 1 and the electrode 2. It is also effective in improving wettability of the surface of the insulating substrate 1 and thickness uniformity during forming the immobilized enzyme layer 4 in which an enzyme is immobilized. It also exhibits selective permeation to ascorbic acid, uric acid and acetaminophen which may interfere with a reaction of hydrogen peroxide on the electrode 2. The binding layer 3 mainly consists of a silane coupling agent. Silane coupling agents which may be used include aminosilanes, vinylsilanes and epoxysilanes. γ-aminopropyltriethoxysilane, an aminosilane, is particularly preferable in the light of adhesiveness and selective permeation. The binding layer 3 may be formed by, for example, spin coating of a silane coupling agent solution, where the concentration of the silane coupling agent is preferably about 1 v/v% (volume %) for significantly improving selective permeability.

The immobilized enzyme layer 4 comprises an organic polymer base material in which a catalytic enzyme is immobilized. The immobilized enzyme layer 4 may be formed by, for example, adding dropwise and applying by spin coating a solution containing some kind of enzyme, a protein cross-linking agent such as glutaraldehyde and albumin on the binding layer 3. Albumin may protect the enzyme from a reaction with the cross-linking agent and may be a protein base material. Enzymes to be immobilized include lactate oxidase, glucose oxidase, urate oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyruvate oxidase, which generate hydrogen peroxide as a product of their catalytic reaction or consume oxygen.

Two or more enzymes may be used in combination for generating hydrogen peroxide; for example any combination of creatininase, creatinase and sarcosine oxidase for allowing creatinine to be detected.

An enzyme may be combined with a coenzyme; for example, a combination of 3-hydroxylactate dehydrogenase and nicotinamide adenine nucleotide (NAD) for allowing 3-hydroxylactic acid to be detected.

An enzyme may be combined with an electron mediator, where an electron mediator which has been reduced by the enzyme is oxidized on the electrode surface to generate a current which is then measured. Such a combination may allow glucose to be detected.

As described above, there are no limitations to the structure of the immobilized enzyme layer 4 as long as it contains at least an enzyme and can convert a target substance into an electrode sensitive substance such as hydrogen peroxide.

There are no limitations to a process for forming the immobilized enzyme layer 4 as long as a uniform layer can be formed; screen printing may be, in addition to spin coating, used.

A fluoroalcohol methacrylate resin composing of the permeation restricting layer 5 is a methacrylate resin whose carboxyl groups are partially or totally esterified by a fluoroalcohol. The fluoroalcohol is an alcohol, one or more or all of whose hydrogens are replaced with fluorine atoms. For example, 1H,1H-perfluorooctyl polymethacrylate or 1H,1H,2H,2H-perfluorodecyl polyacrylate may be used. In this invention, for example, 1H,1H-perfluorooctyl polymethacrylate is a polymer in which methacrylic acid moieties are partially or totally esterified by 1H,1H-perfluorooctylalcohol.

The permeation restricting layer 5 may be formed by adding dropwise and applying by spin coating a solution of a fluoroalcohol methacrylate resin in a perfluorocarbon solvent such as perfluorohexane on the immobilized enzyme layer 4 in which a catalytic enzyme is immobilized.

Figure 6:
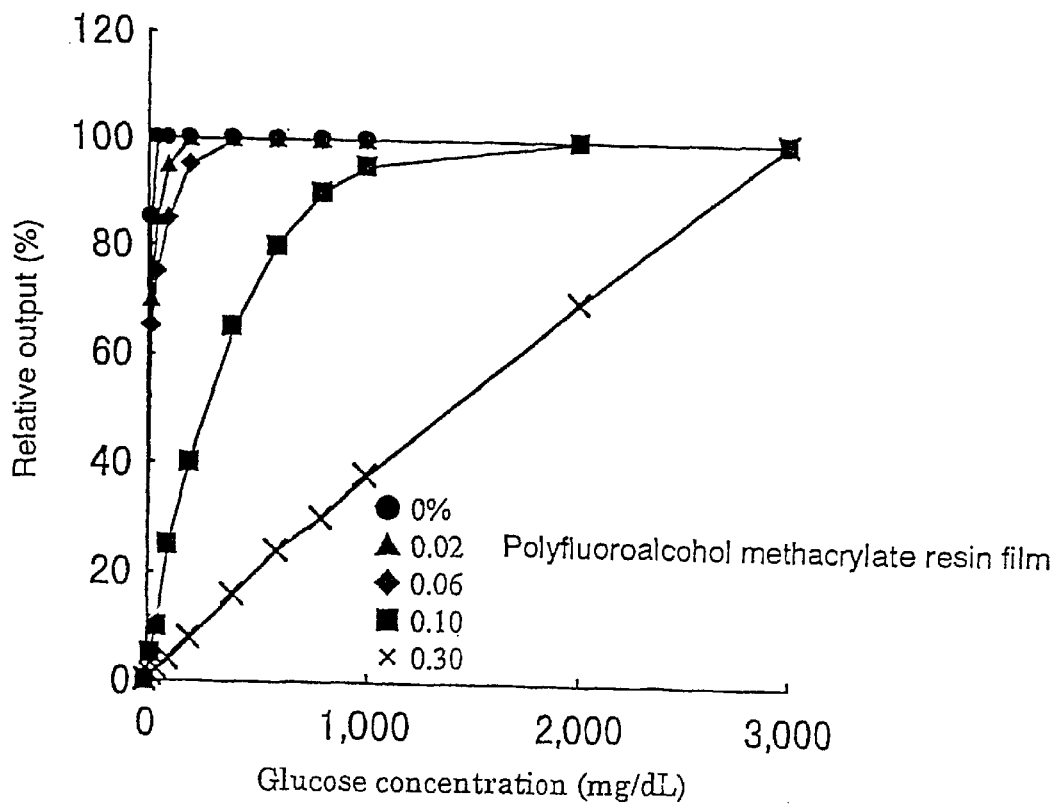
FIG. 6 shows a relationship between a sensor output in a sensor according to this invention and a concentration of a methacrylate-resin fluoroalcohol ester.

The concentration of the fluoroalcohol methacrylate resin in the solution may be preferably 0.1 to 5 wt %, more preferably about 0.3 wt %, depending on a target substance because a concentration within the range may, as described later, provide good permeation-restricting property (FIG. 6).

There are no limitations to a process for forming the permeation restricting layer 5 as long as a uniform layer may be formed; spray coating or dipping may be, in addition to spin coating, employed.

When the enzyme electrode of this embodiment is used as a glucose sensor, the outermost permeation restricting layer 5 restricts a diffusion rate of glucose and an organic polymer film 4 containing glucose oxidase catalytically reacts diffused glucose with oxygen to generate hydrogen peroxide and gluconolactone. A current generated when the hydrogen peroxide reaches the electrode 2 may be measured to determine a level of glucose. For an electrode system during measurement, a conventional external reference electrode is used in a two-electrode system, while both a counter electrode and a reference electrode are soaked in a measured solution at the same time for a three-electrode system.

Embodiment 2

Figure 2:
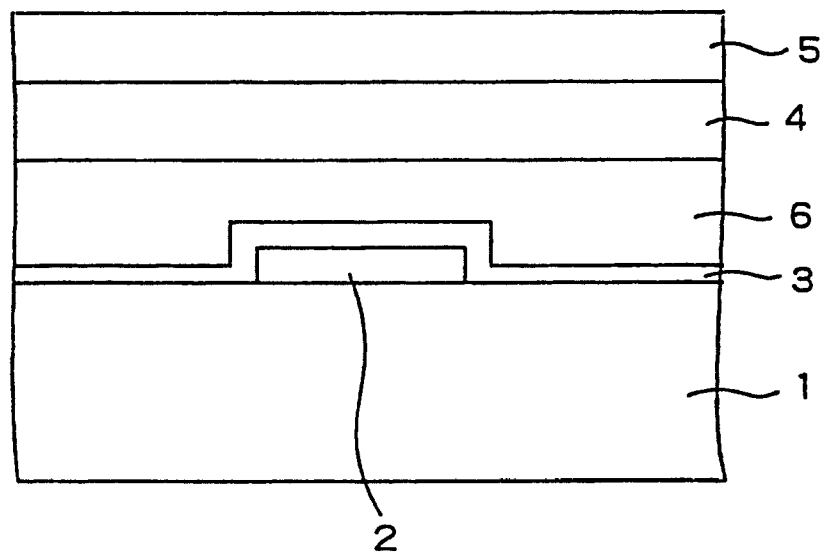
FIG. 2 is a cross section of another embodiment of an enzyme electrode according to this invention.

This embodiment will be described with reference to FIG. 2. The enzyme electrode of this embodiment comprises an electrode 2 as a working electrode on an insulating substrate 1, on which a binding layer 3 mainly consisting of γ-aminopropyltriethoxysilane is formed. On the binding layer are sequentially formed an ion-exchange polymer layer 6 mainly consisting of a perfluorocarbon-sulfonate acid polymer(NAFION), an immobilized enzyme layer 4 in which a catalytic enzyme is immobilized in an organic polymer, and a permeation restricting layer 5 consisting of a fluoroalcohol methacrylate resin.

The electrode 2 and the γ-aminopropyltriethoxysilane film 3 on the insulating substrate 1 are sequentially formed as described in Embodiment 1.

The ion-exchange polymer layer 6 mainly consisting of a perfluorocarbon-sulfonate acid polymer(NAFION) may be formed by, for example, adding dropwise and applying by spin coating a solution of a perfluorocarbon-sulfonate acid polymer in pure water and ethanol (50:50) on the binding layer 3 consisting of γ-aminopropyltriethoxysilane. The solvent may be an alcohol such as isopropyl alcohol and ethanol. The concentration of the perfluorocarbon-sulfonate polymer is preferably 1 to 10 w/v%, more preferably 5 to 7 w/v% because a concentration within the range may significantly contribute to eliminating influence of ascorbic acid interfering with an electrode reaction of hydrogen peroxide.

Embodiment 3

Figure 3:
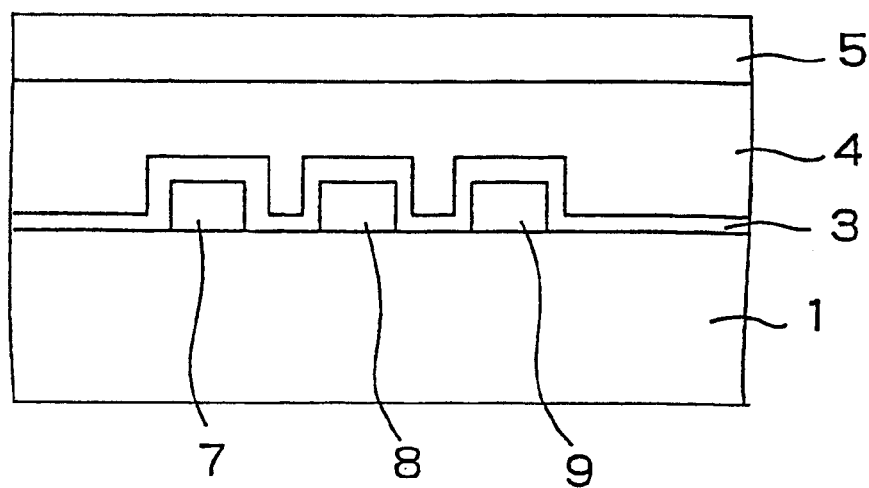
FIG. 3 is a cross section of another embodiment of an enzyme electrode according to this invention.

This embodiment will be described with reference to the drawings. As shown in FIG. 3, the enzyme electrode of this embodiment comprises a working electrode 7, a counter electrode 8 and a reference electrode 9 on an insulating substrate 1, on which a binding layer 3 mainly consisting of γ-aminopropyltriethoxysilane is formed. On the binding layer are sequentially formed an immobilized enzyme layer 4 in which a catalytic enzyme is immobilized in an organic polymer, and a permeation restricting layer 5 consisting of a fluoroalcohol methacrylate resin. The materials for the working electrode 7 and the counter electrode 8 may be as described for the electrode 2 in Embodiments 1 and 2. The reference electrode 9 may be made of silver/silver chloride.

Such a structure may allow a solution to be replaced while operating a sensor because the working electrode, the counter electrode and the reference electrode are formed on the single insulating substrate since the working electrode, the counter electrode and the reference electrode are electrically connected with each other as long as the surface of the sensor is wet and thus measurement can be continued even when the sensor is temporarily in contact with the air. It also allows precise electrochemical measurement by a three-electrode system. In particular, it may provide a small amperometric detection type of enzyme electrode. Furthermore, an ion-exchange polymer layer 6 consisting of a perfluorocarbon-sulfonate acid polymer may be formed between the γ-aminopropyltriethoxysilane film 3 and the immobilized enzyme layer 4 as described in Embodiment 2.

Embodiment 4

Figure 4:
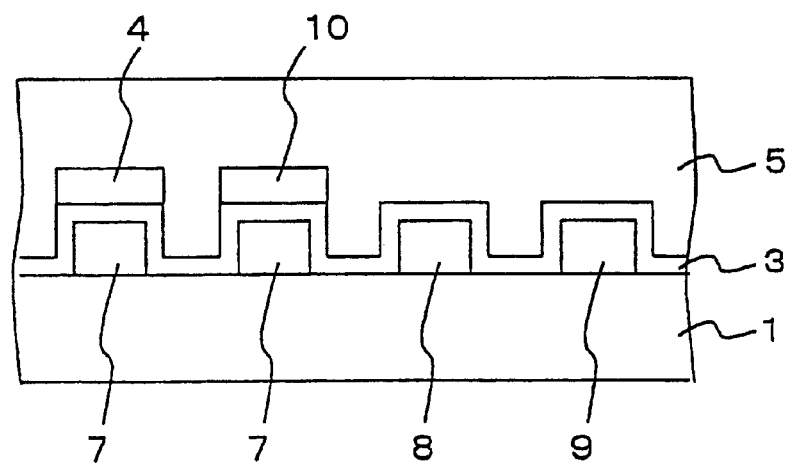
FIG. 4 is a cross section of another embodiment of an enzyme electrode according to this invention.

This embodiment will be described with reference to the drawings. As shown in FIG. 4, the enzyme electrode of this embodiment comprises two working electrodes 7, a counter electrode 8 and a reference electrode 9 on an insulating electrode 1, on which a binder layer 3 mainly consisting of γ-aminopropyltriethoxysilane is formed. On these working electrodes 7 are formed immobilized enzyme layers 4, 10 in which a different type of enzyme is immobilized, on which further a permeation restricting layer 5 consisting of a fluoroalcohol methacrylate resin is formed. The materials for the working electrodes 7 and the counter electrode 8 may be as described for the electrode 2 in Embodiments 1 and 2. The reference electrode 9 is preferably made of silver/silver chloride.

Such a configuration comprises layers in which a differently catalytic enzyme is formed, on two working electrodes, allowing a plurality of particular ingredients in a sample at the same time.

Embodiment 5

This embodiment is an example of a process for manufacturing an enzyme electrode according to this invention.

First, a working electrode of platinum and a counter electrode and a reference electrode of silver/silver chloride are formed on a substrate of quartz.

Then, the surfaces of each electrode and of the substrate are washed. The process may be conducted with, for example, an organic solvent or acid, an ultrasonic cleaner or combination thereof. A solvent or acid used should not cause damage to the electrode materials. The organic solvent is preferably a polar solvent; for example, ketones such as acetone and alcohols such as isopropyl alcohol. The acid is, for example, diluted sulfuric acid. Electrolysis cathode water, which is a solution generated around a cathode during electrolysis of pure water, may be used. Electrolysis cathode water is neutral to weakly alkaline and highly reductive, so that it can minimize damage to the substrate and the electrodes while making the potentials on the surfaces of the substrate and of adhered particles negative, to prevent detached particles from re-adhesion. Among the above procedures, a process of sequentially washing with acetone and sulfuric acid is preferable.

Then, a binding layer is formed on the working electrodes, the counter electrode and the reference electrode. As described above, the binding layer may be preferably made of a silane coupling agent such as γ-aminopropyltriethoxysilane.

A coupling agent may be applied by, for example, spin coating, spraying, dipping and a hot stream method. Spin coating is a process that a solution or suspension of components for a binding layer such as a coupling agent is applied with a spin coater, by which a thinner binding layer may be formed, adequately controlling its thickness. Spraying is a process that for example, a solution of a coupling agent is sprayed on a substrate and dipping is a process that a substrate is soaked into, for example, a solution of a coupling agent. By these process, a binding layer may be formed by simple steps without no special apparatuses. A hot stream method is a process that for example, a stream of a coupling agent solution is flown over a substrate at an elevated temperature, by which a thinner binding layer may be formed, adequately controlling its thickness.

After applying the coupling agent solution, the substrate is dried generally, but not limited to, at an ambient temperature (25° C.) to 170° C., for 0.5 to 24 hours depending on the temperature. Drying may be conducted in the air or in an inert gas such as nitrogen; for example, a nitrogen blowing may be employed, in which nitrogen is blown on the substrate to be dried.

An enzyme solution is applied on the binding layer thus formed, to form an immobilized enzyme layer. The enzyme layer may be applied by, for example, spin coating or dipping (soaking), particularly spin coating because of its thickness controllability. After applying the enzyme solution, the substrate is dried at a temperature which does not impair enzyme activity, preferably an ambient temperature (25° C.) to 40° C., for 0.5 to 24 hours depending on the drying temperature. Drying may be conducted in the air or in an inert gas such as nitrogen; for example, a nitrogen blowing may be employed, in which nitrogen is blown on the substrate to be dried.

Then, on the substrate is applied, for example, a solution of a polycarboxylic acid fluoroalcohol ester to form a permeation restricting layer, by, for example, spin coating, dipping, spraying or brush coating, preferably spin coating because of its thickness controllability. By spin coating, a permeation restricting layer as a film about 0.01 to 3 μm of thickness may be formed, adequately controlling its thickness. Alternatively, the substrate is soaked into the above solution by dipping for application thereof, and is then dried by nitrogen blowing, by which a permeation restricting layer may be formed by a simple process.

After applying the solution, the substrate is dried at a temperature which does not impair enzyme activity, preferably an ambient temperature (25° C.) to 40° C., for 0.5 to 24 hours depending on the drying temperature. Drying may be conducted in the air or in an inert gas such as nitrogen; for example, a nitrogen blowing may be employed, in which nitrogen is blown on the substrate to be dried.

As described above, an enzyme electrode may be manufactured, in which a variety of layers with particular functions are formed on an electrode. This embodiment shows a process that a binding layer, an immobilized enzyme layer and a permeation restricting layer are formed on all of working electrodes, a counter electrode and a reference electrode, but this invention is not limited to the configuration. It is, for example, possible to form a binding layer, an immobilized enzyme layer and a permeation restricting layer on working electrodes and a counter electrode while forming a binder layer on a reference layer and then a protection layer for protecting the reference layer. Although this embodiment shows a three-electrode system of biosensor comprising working electrodes, a counter electrode and a reference electrode, a configuration that a working electrode of platinum and a reference electrode are formed on a quartz substrate may be acceptable.

Embodiment 6

Figure 16:
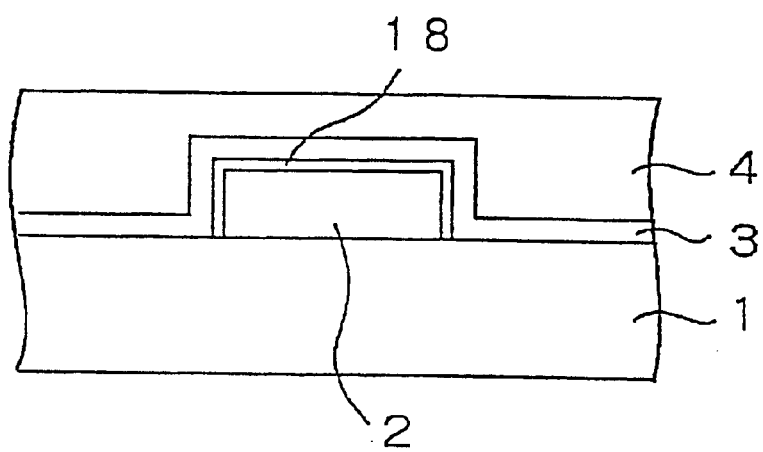
FIG. 16 is a cross section of an enzyme electrode according to this invention.

This embodiment will be described with reference to the drawings. The enzyme electrode of this embodiment, as shown in FIG. 16, comprises an electrode 2 as a working electrode on an insulating substrate 1, and an electrode protection layer 18 mainly consisting of an urea compound which covers the surface of the electrode. The electrode protection layer 18 is selectively formed on the surface of the electrode 2. On the overall surface are formed a binding layer 3 mainly consisting of γ-aminopropyltriethoxysilane and then an immobilized enzyme layer 4 in which an enzyme is immobilized in an organic polymer as a base material.

The insulating substrate 1 may mainly consisting of a highly-insulative material such as ceramics, glass, quartz and plastics, which is preferably excellent in waterproof, heat resistance, chemical resistance and adhesiveness to an electrode.

The electrode 2 may mainly consist of a material such as platinum, gold, silver and carbon; platinum is particularly preferable because of its excellent chemical resistance and detection property for hydrogen peroxide. The electrode 2 on the insulating substrate 1 may be formed by, for example, spattering, ion plating, vacuum deposition, chemical paper deposition and electrolysis; spattering is particularly preferable because the electrode 2 is highly adhesive to the insulating substrate 1 and a platinum layer can be easily formed. Furthermore, a titanium or chromium layer may be inserted between these layers for improving adhesiveness of the insulating substrate 1 to the electrode 2.

The electrode protection layer 18 covering the electrode 2 restricts permeation of contaminants such as urea contained in a sample to the electrode. The electrode protection layer 18 comprises an urea compound such as, but not limited to, urea and thiourea, preferably urea because of its lower toxicity and lower cost. The enzyme electrode of this embodiment comprises the electrode protection layer containing a contaminant on the surface of the electrode for preventing variation of sensitivity due to contamination during operation. It will be, therefore, readily understood in the light of the function of the electrode protection layer that the urea compound is not limited to the above specific examples.

The electrode protection layer 18 may be formed by, for example, dipping, plasma polymerization and electrolysis, preferably electrolysis which may be conducted with an inexpensive apparatus for a reduced process time. Specifically, it is preferable to form an electrode protection layer by soaking an insulating substrate on which an electrode has been formed into a mixed solution containing a supporting electrolyte and an urea compound and applying electricity to the solution, where the concentration of urea in the mixed solution is preferably 0.1 mM to 6.7 M, more preferably 1 M to 6.7 M. The concentration of sodium chloride in the mixed solution is preferably 0.1 mM to 2 M, more preferably 1.5 mM to 150 mM. Thus, there may be provided a high-quality electrode protection layer which can effectively restrict adhesion of contaminants to the electrode and restrict permeation of interferent substances for good selectivity. It may improve adhesiveness to the binding layer 3 mainly consisting of γ-aminopropyltriethoxysilane.

The binding layer 3 on the electrode protection layer 18 may improve adhesiveness (binding strength) of the immobilized enzyme layer 4 thereon to the insulating substrate 1 and the electrode protection layer 18. It is also effective in improving wettability of the surface of the insulating substrate 1 and thickness uniformity during forming the immobilized enzyme layer 4 in which an enzyme is immobilized. It also exhibits selective permeation to ascorbic acid, uric acid and acetaminophen which may interfere with a reaction of hydrogen peroxide on the electrode 2. The binding layer 3 mainly consists of a silane coupling agent. Silane coupling agents which may be used include aminosilanes, vinylsilanes and epoxysilanes. y-aminopropyltriethoxysilane, an aminosilane, is particularly preferable in the light of adhesiveness and selective permeation. The binding layer 3 may be formed by, for example, spin coating of a silane coupling agent solution, where the concentration of the silane coupling agent is preferably about 1 v/v% (volume %) for significantly improving selective permeability.

The immobilized enzyme layer 4 comprises an organic polymer base material in which a catalytic enzyme is immobilized. The immobilized enzyme layer 4 may be formed by, for example, adding dropwise and applying by spin coating a solution containing some kind of enzyme, a protein cross-linking agent such as glutaraldehyde and albumin on the binding layer 3. Albumin may protect the enzyme from a reaction with the cross-linking agent and may be a protein base material. Enzymes to be immobilized include lactate oxidase, glucose oxidase, urate oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyruvate oxidase, which generate hydrogen peroxide as a product of their catalytic reaction or consume oxygen.

Two or more enzymes may be used in combination for generating hydrogen peroxide; for example any combination of creatininase, creatinase and sarcosine oxidase for allowing creatinine to be detected.

An enzyme may be combined with a coenzyme; for example, a combination of 3-hydroxylactate dehydrogenase and nicotinamide adenine nucleotide (NAD) for allowing 3-hydroxylactic acid to be detected.

An enzyme may be combined with an electron mediator, where an electron mediator which has been reduced by the enzyme is oxidized on the electrode surface to generate a current which is then measured. Such a combination may allow glucose to be detected.

As described above, there are no limitations to the structure of the immobilized enzyme layer 4 as long as it contains at least an enzyme and can convert a target substance into an electrode sensitive substance such as hydrogen peroxide.

There are no limitations to a process for forming the immobilized enzyme layer 4 as long as a uniform layer can be formed; screen printing may be, in addition to spin coating, used.

Embodiment 7

Figure 17:
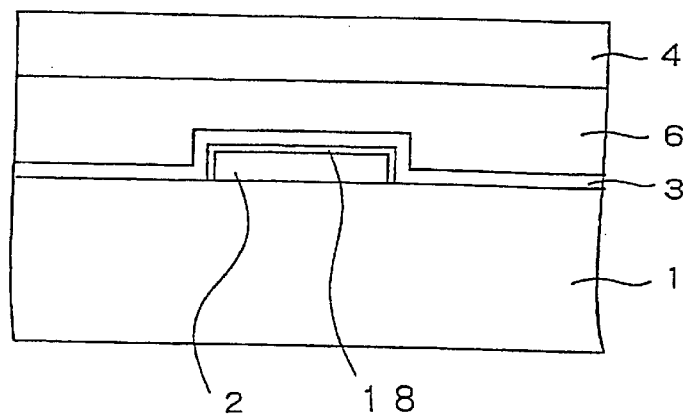
FIG. 17 is a cross section of an enzyme electrode according to this invention.

This embodiment will be described with reference to the drawings. The enzyme electrode of this embodiment, as shown in FIG. 17, comprises an electrode 2 as a working electrode on an insulating substrate 1, and an electrode protection layer 18 mainly consisting of an urea compound which covers the surface of the electrode. On the overall surface are sequentially formed a binding layer 3 mainly consisting of y-aminopropyltriethoxysilane, an ion-exchange polymer layer 6 consisting of a perfluorocarbon-sulfonate acid polymer and an immobilized enzyme layer 4 in which an enzyme is immobilized in an organic polymer as a base material.

The electrode 2, the electrode protection layer 18, the y-aminopropyltriethoxysilane layer 3 and the immobilized enzyme layer 4 are sequentially formed on the insulating substrate 1 as described in Embodiment 1.

The perfluorocarbon-sulfonate polymer composing of the ion-exchange polymer layer 6 may be, for example, NAFION, which is a cation-exchange polymer in which perfluoroalkylene ether side chains having a terminal sulfonic group are attached to a perfluoromethylene principal chain (Formula 1).

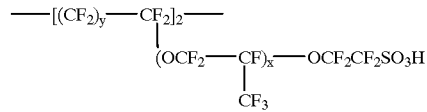

FORMULA 1

The ion-exchange layer 6 such as a NAFION film disposed on the immobilized enzyme layer may eliminate influence of interferent substances, which may be synergic with the permeation-restricting effect of the electrode protection layer 3 to interferent substances to significantly minimize the influence of interferent substances.

The ion-exchange polymer layer 6 may be formed by adding dropwise and applying by spin coating a solution of NAFION in pure water and ethanol (50:50) on the γ-aminopropyltriethoxysilane layer 3. The solvent may be an alcohol such as isopropyl alcohol and ethanol. The concentration of NAFION is preferably 1 to 10 w/v%, more preferably 5 to 7 w/v% because a concentration within the range may significantly contribute to eliminating the influence of interferent substances.

Embodiment 8

Figure 18:
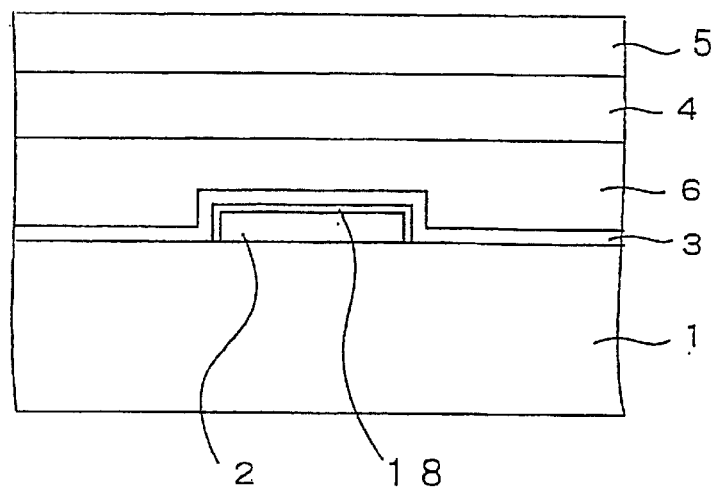
FIG. 18 is a cross section of an enzyme electrode according to this invention.

This embodiment will be described with reference to the drawings. The enzyme electrode of this embodiment, as shown in FIG. 18, comprises an electrode 2 as a working electrode on an insulating substrate 1, and an electrode protection layer 18 mainly consisting of an urea compound which covers the surface of the electrode. On the overall surface are sequentially formed a binding layer 3 mainly consisting of γ-aminopropyltriethoxysilane, an ion-exchange polymer layer 6 consisting of a perfluorocarbon-sulfonate acid polymer, an immobilized enzyme layer 4 in which an enzyme is immobilized in an organic polymer as a base material and a permeation restricting layer 5 as the uppermost layer. The electrode 2, the electrode protection layer 18, the γ-aminopropyltriethoxysilane layer 3, the ion-exchange polymer layer 6 consisting of a perfluorocarbon-sulfonate polymer and the immobilized enzyme layer 4 in which an enzyme is immobilized are sequentially formed on the insulating substrate 1 as described in Embodiments 1 and 2.

The permeation restricting layer 5 may be made of a polymer in which a pendant group containing at least a fluoroalkylene block is attached to a non-fluorinated vinyl polymer. The permeation restricting layer 5 may be formed by applying by spin coating the above polymer solution. For example, a solution of a fluoroalcohol polymethacrylate in a perfluorocarbon solvent such as perfluorohexane may be added dropwise and applied by spin coating on the immobilized enzyme layer 4 in which a catalytic enzyme is immobilized. The ester concentration in the solution may be preferably 0.1 to 5 wt %, more preferably about 0.3 wt %, depending on a target substance because a concentration within the range may, as described later, provide good permeation-restricting property.

There are no limitations to a process for forming the permeation restricting layer 5 as long as a uniform layer may be formed; spray coating or dipping may be, in addition to spin coating, employed.

The permeation restricting layer 5 consisting of a polymer having the particular structure may prevent adhesion of contaminants such as proteins and urea compounds, which is synergic with prevention of contaminant adhesion by the electrode protection layer 3, leading to stable output properties even for a long-term use. Furthermore, it may provide good permeation restricting- property, resulting in significant extension of measurable concentration range. Furthermore, good adhesiveness between the permeation-restriction layer 5 and the immobilized enzyme layer 4 may permit to consistently measure a target substance in a solution for a long time and to consistently measure an ionized substance such as lactic acid because the permeation restricting layer has no charges and therefore little interacts with an ionic substance.

When the sensor of this embodiment is used as a glucose sensor, the outermost permeation restricting layer 5 restricts a diffusion rate of glucose and an immobilized enzyme layer 4 containing glucose oxidase catalytically reacts diffused glucose with oxygen to generate hydrogen peroxide and gluconolactone. A current generated when the hydrogen peroxide reaches the electrode 2 may be measured to determine a level of glucose. For an electrode system during measurement, a conventional external reference electrode is used in a two-electrode system, while both a counter electrode and a reference electrode are soaked in a measured solution at the same time for a three-electrode system.

Embodiment 9

Figure 19:
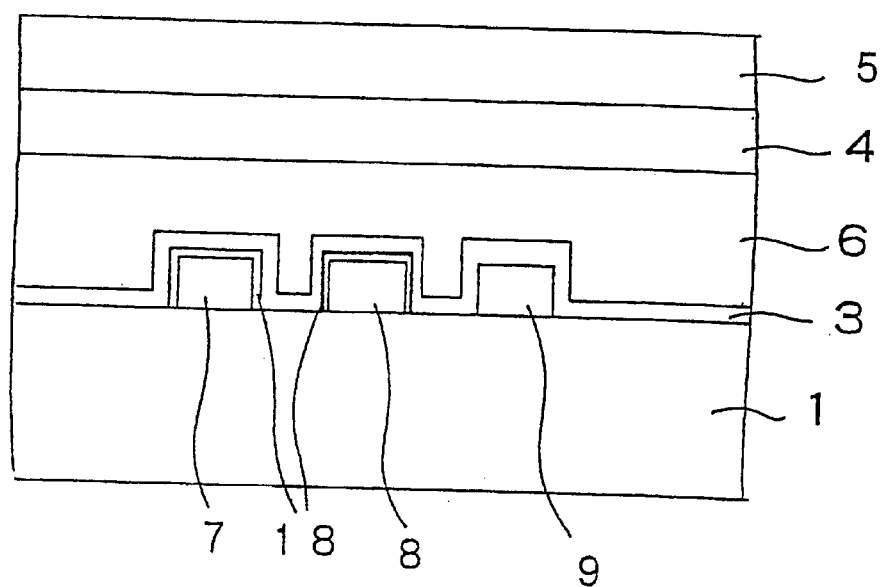
FIG. 19 is a cross section of an enzyme electrode according to this invention.

This embodiment will be described with reference to the drawings. The enzyme electrode of this embodiment, as shown in FIG. 19, comprises a working electrode 7, a counter electrode 8 and a reference electrode 9. On the working electrode 7 and the counter electrode 8 are sequentially formed an electrode protection layer 18, a binding layer 3 mainly consisting of γ-aminopropyltriethoxysilane, an ion-exchange polymer layer 6 mainly consisting of a perfluorocarbon-sulfonate polymer, an immobilized enzyme layer 4 in which a catalytic enzyme is immobilized and a permeation restricting layer 7. The materials for the working electrode 7 and the counter electrode 8 may be the same as that for the electrode 2. The reference electrode 9 may be made of silver/silver chloride.

Such a structure may allow a solution to be replaced while operating a sensor because the working electrode, the counter electrode and the reference electrode are formed on the single insulating substrate since the working electrode, the counter electrode and the reference electrode are electrically connected with each other as long as the surface of the sensor is wet and thus measurement can be continued even when the sensor is temporarily in contact with the air. It also allows precise electrochemical measurement by a three-electrode system. In particular, it may provide a small amperometric detection type of enzyme electrode.

Embodiment 10

Figure 28A:
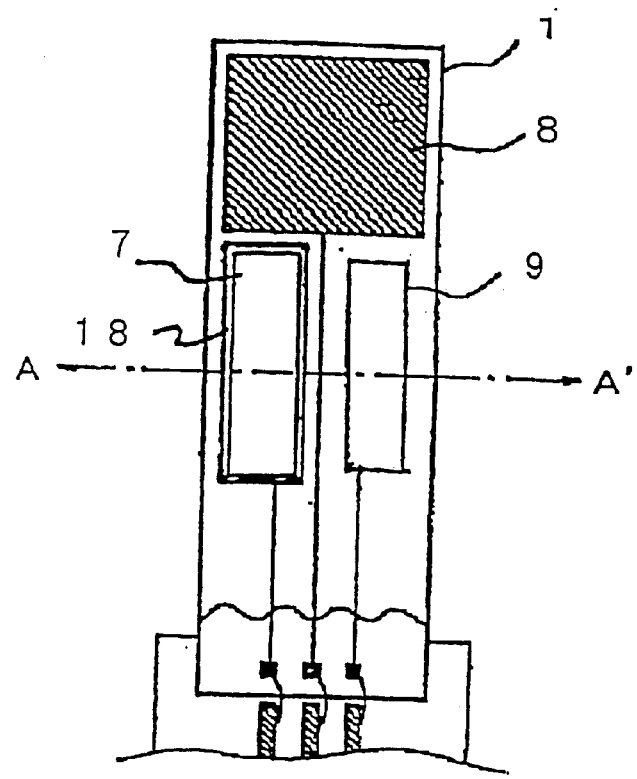
FIG. 28(a) is a schematic view of a biosensor according to this invention.
Figure 28B:
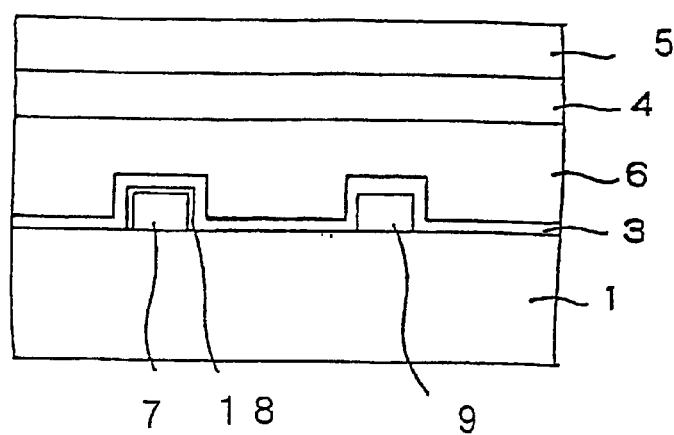
FIG. 28(b) is cross-section A–A' from FIG. 28(a).

FIG. 28 shows a sensor employing an enzyme electrode according to this invention. In the embodiment, a working electrode 7 is an enzyme electrode and a counter electrode 8 and a reference electrode 9 are formed on a quartz substrate. The working electrode 7 and the counter electrode 8 are made of platinum while the reference electrode 9 is made of silver/silver chloride. The working electrode 7 is completely covered by an electrode protection layer 18 consisting of urea, on which are sequentially formed a binding layer 3 mainly consisting of γ-aminopropyltriethoxysilane, an ion-exchange polymer layer 6 consisting of NAFION, an immobilized enzyme layer 4 and a permeation restricting layer 5 consisting of a fluoroalcohol methacrylate resin. The working electrode 7, the counter electrode 8 and the reference electrode 9 are connected to corresponding measuring systems, respectively.

Figure 29:
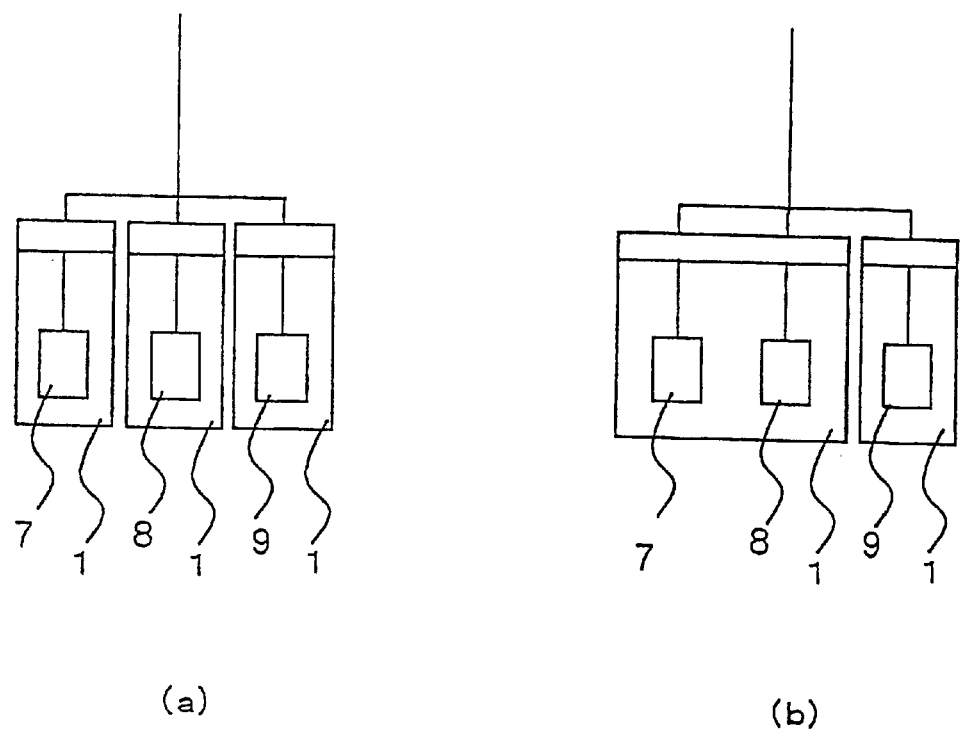
FIGS. 29(a) and (b) show configuration examples of a biosensor according to this invention.

In this embodiment, the working electrode 7, the counter electrode 8 and the reference electrode 9 are formed on the single insulating substrate 1, but these electrodes may be formed on multiple substrates. FIG. 29(*a*) shows a configuration where a working electrode 7, a counter electrode 8 and a reference electrode 9 are separately formed on different insulating substrates 1, while FIG. 29(*b*) shows a configuration where a working electrode 7 and a counter electrode 8 are formed on the same insulating substrate 1 and a reference electrode 9 is on another insulating substrate 1.

These figures show examples of an amperometric type of sensor, but the enzyme electrode of this invention may be, of course, applied to an ion-sensitive field effect transistor type of sensor.

Embodiment 11

This embodiment is an example of a measuring apparatus according to this invention equipped with a biosensor, an electrochemical measuring circuit, a data processor and a data indicator, which will be described with reference to FIGS. 31 and 32.

Figure 31:
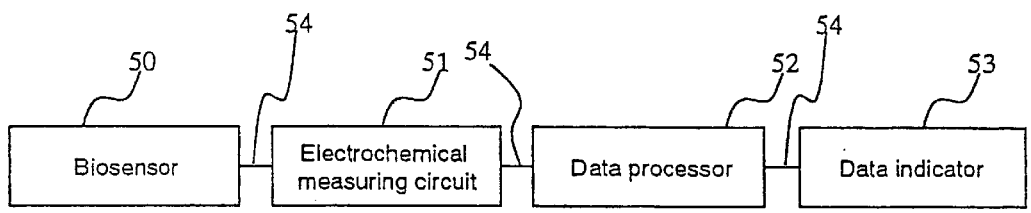
FIG. 31 shows a configuration example of a measuring apparatus according to this invention.

The measuring apparatus, as shown in FIG. 31, comprises a biosensor 50, an electrochemical measuring circuit 51, a data processor 52 and a data indicator 53, which are connected by wirings 54.

The biosensor 50 may comprises an enzyme electrode, for example, described in any of Embodiments 1 to 4. Since the biosensor 50 is consumable, it is preferably removable for facilitating replacement.

The electrochemical measuring circuit 51 is a potentiostat in this embodiment, but it may be any circuit which may apply a constant potential to the biosensor 50 to determine a current value.

Figure 32:
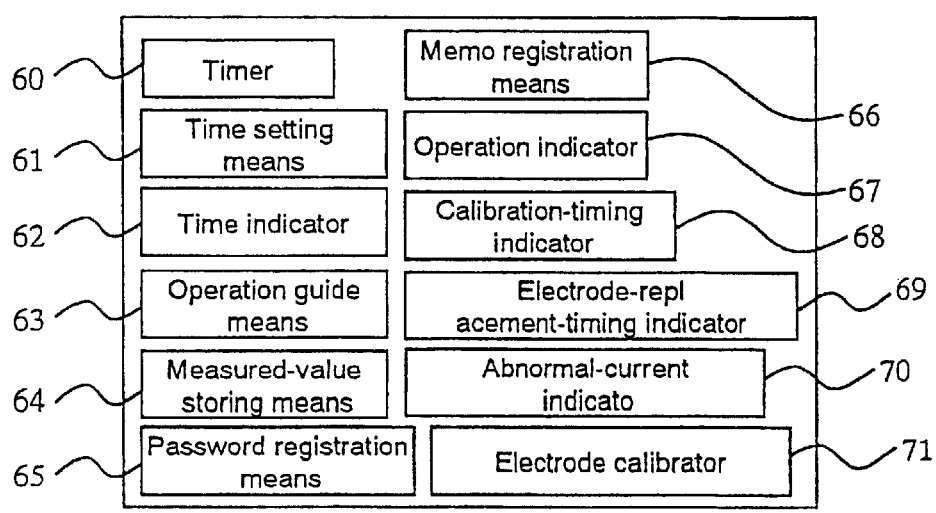
FIG. 32 shows a configuration example of a data processor in a measuring apparatus according to this invention.

The data processor 52 has a configuration shown in FIG. 32, comprising a timer 60, a time setting means 61, a time indicator 62, an operation guide means 63, a measured-value storing means 64, a password registration means 65, a memo registration means 66, an operation indicator 67, a calibration-timing indicator 68, an electrode-replacement-timing indicator 69, an abnormal-current indicator 70 and an electrode calibrator 71. The processor comprising these means may allow an operator to smoothly conduct calibration of the electrode, measurement and storage of measurement data. Although this embodiment has a personal computer (hereinafter, referred to as a "PC") as a data processor 52, it may be any apparatus having an operation unit such as a microprocessor which may process a signal from the electrochemical circuit 51. A signal processed by the data processor 52 is converted into a measured value, which is then indicated by the data indicator 53.

In this embodiment, the data indicator 53 is a display for PC, but it may be any apparatus which may indicate data processed by the data processor 52. The data processed by the data processor 52 may include a measured value calculated by the data processor 52, status (normal or malfunction) of the biosensor 50, detection results for an abnormal current value, a timing for replacing the biosensor 50, a timing and a procedure for calibration of the biosensor 50, a date, a time, a clock, a signal from the electrochemical measuring circuit 51 which is processed by the operation unit in the data processor 52, instructions for operation means for initial setting, and instructions giving an advice during operation. An indicating means may be a digital number, an analogue number or voice. Other indicating means may include beep, light, vibration, color, graphic and heat, but a digital or analogue number is preferable.

The wiring 54 may be any electric wire which can connect these.

Next, each means in the data processor 52 (FIG. 32) will be described.

The timer 60 is a clock built in a PC, but it may be any type giving a time to the operation unit.

The time setting means 61 sets a time when a measurement is performed, using the timer 60. In this embodiment, the means utilizes some functions of the clock built in the PC as is for the timer 60, but it may be any type which can give a time to the operation unit as well as set a time of measurement. It is preferable that a plurality of times can be set for facilitating multiple measurements a day. It may be more convenient that an operator can select whether using the time setting means 61 or not.

The time indicator 62 indicates a time set by the time setting means 61. For example, the time setting means 61 set to indicate a time every 12 hours allows an operator to know a measuring time every 12 hours from the time indicator 62.

The operation guide means 63 describes an operation procedure for a measuring apparatus or instructions for operation. Use of the operation guide means 63 can be selected by setting as appropriate.

The measured-value storing means 64 stores a measured value from the measuring apparatus or other information. Its semiconductor storage element is preferably a RAM (random access memory). The measured-value storing means 64 can preferably store a plurality of measured values. The measured-value storing means 64 can store not only a measured value, but also a variety of information to be processed by the data processor 52. Data to be stored can be controlled by setting as appropriate.

The password registration means 65 controls use of the measuring apparatus by an individual other than a particular operator and data on measured values for allowing user's privacy to be protected. A password is preferably constructed with a four or more digit number or alphanumeric for ensuring higher security. The password registration means 65 can preferably register a plurality of passwords for protecting two or more users' privacy. In this embodiment, any data cannot be input/output without a four digit password although use of the password registration means 65 can be appropriately selected by setting.

Preferably, the memo registration means 66 comprises a memo register for registering a memo, a memo itemizing means for accessing a registered memo group, a memo selector for selecting a memo item to be registered from the accessed memo group and a memo access means for accessing the memo selected by the memo selector. In this embodiment, the memo registration means having the configuration can register subject's data such as weight, blood pressure and temperature at measurement. Use of the memo registration means 66 can be appropriately selected by setting.

The operation indicator 67 indicates a status when one or both of the wirings 54 between the biosensor 50 and the electrochemical measuring circuit 51 and between the electrochemical measuring circuit 51 and the data processor 52 are disconnected. Use of the operation indicator 67 can be appropriately selected by setting.

The calibration-timing indicator 68 indicates a timing for calibration of the biosensor 50. After being used to a certain extent, an enzyme electrode should be calibrated. Thus, the calibration timing indicator 68 indicates a calibration timing. The timing may be determined, based on an accumulated measuring time or the number of measurement. In this embodiment, one or both of the criteria can be selected as criteria for calibration, by setting.

The electrode-replacement-timing indicator 69 indicates timing for replacing an electrode in the biosensor 50. The timing may be determined, based on some criteria such as an accumulated measuring time, the number of measurement and voltage drop in a battery. In this embodiment, one or all of the factors can be selected as criteria for calibration, by setting.

The abnormal-current indicator 70 indicates a status when measurement cannot be conducted due to an abnormal current passing through the biosensor 50, the electrochemical measuring circuit 51, the data processor 52 and/or the wirings 54 connecting these or when some of these elements are broken.

"Indication" in the operation indicator 67, the calibration-timing indicator 68, the electrode-replacement-timing indicator 69 and the abnormal current indicator 70 may be, for example, performed through the above data indicator to inform certain data of a measuring apparatus operator.

The electrode calibrator 71 is used during an initial stage of use or calibration. It can indicate a calibration procedure for the biosensor 50 and calibrate the biosensor 50. The calibration procedure may be indicated through the calibration-timing-indicator 68.

The measuring apparatus of this embodiment indicates various data such as the lifetime of a biosensor, a timing of calibration and an operation procedure for the device, so that even an unfamiliar individual can conduct precise measurement.

Although this embodiment has a configuration where the biosensor 50, the electrochemical measuring circuit 51, the data processor 52 and the data indicator 53 are connected via the wirings 54, an alternative configuration may be employed, in which an electrochemical measuring circuit 51 and a data indicator 53 are directly connected without a data processor 52. In such a configuration, an analogue signal from the biosensor 50 is directly sent to the data indicator 53, which then indicates a measured value via, for example, an indicating system of a graduation and a pointer. It may be helpful to provide a table for converting an indicated value into an urinary-sugar or blood-sugar value.

Embodiment 12

This embodiment relates to a measuring apparatus as shown in FIG. 31 which is further equipped with a temperature sensor 56 and a pH sensor 57. It will be described with reference to FIG. 33.

Figure 33:
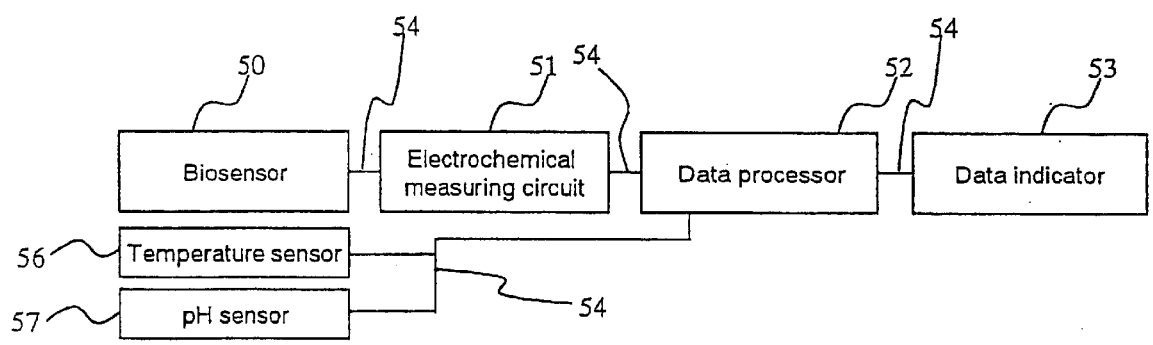
FIG. 33 shows a configuration example of a measuring apparatus according to this invention.

As shown in FIG. 33, the measuring apparatus comprises a biosensor 50, an electrochemical measuring circuit 51, a data processor 52, a data indicator 53, a temperature sensor 56 and a pH sensor 54, which are connected via wirings 54.

The data processor 52 processes an electric signal from the temperature sensor 56 and the pH sensor 57 to calculate the temperature and the pH. Then, a measured value for a particular component in a sample estimated in the data processor 52 is corrected on the basis of the temperature and the pH to indicate the corrected data by the data indicator 53.

The temperature sensor 56 may be any type which can provide a form of data processable by the data processor 52, preferably a thermoelectric thermometer or resistance thermometer. The temperature sensor 56 measures a sample or ambient temperature. When measuring a sample temperature, the temperature sensor 56 is formed on the substrate comprising the biosensor using an enzyme electrode, for precisely determining the sample temperature and accurately correcting a measured value in detecting a particular component in the sample. When the measuring apparatus has the biosensor and the temperature sensor separately, these sensors may be soaked in the sample at the same time, for eliminating necessity for replacing the temperature sensor and the biosensor as one unit, leading to cost reduction. When measuring an ambient temperature, the temperature sensor 56 separately formed from the biosensor is placed in an ambient. The temperature sensor 56 is placed, for example, within the data indicator 53 or the electrochemical measuring circuit 51, for facilitating monitoring whether the ambient temperature is within measurable limits.

Figure 15:
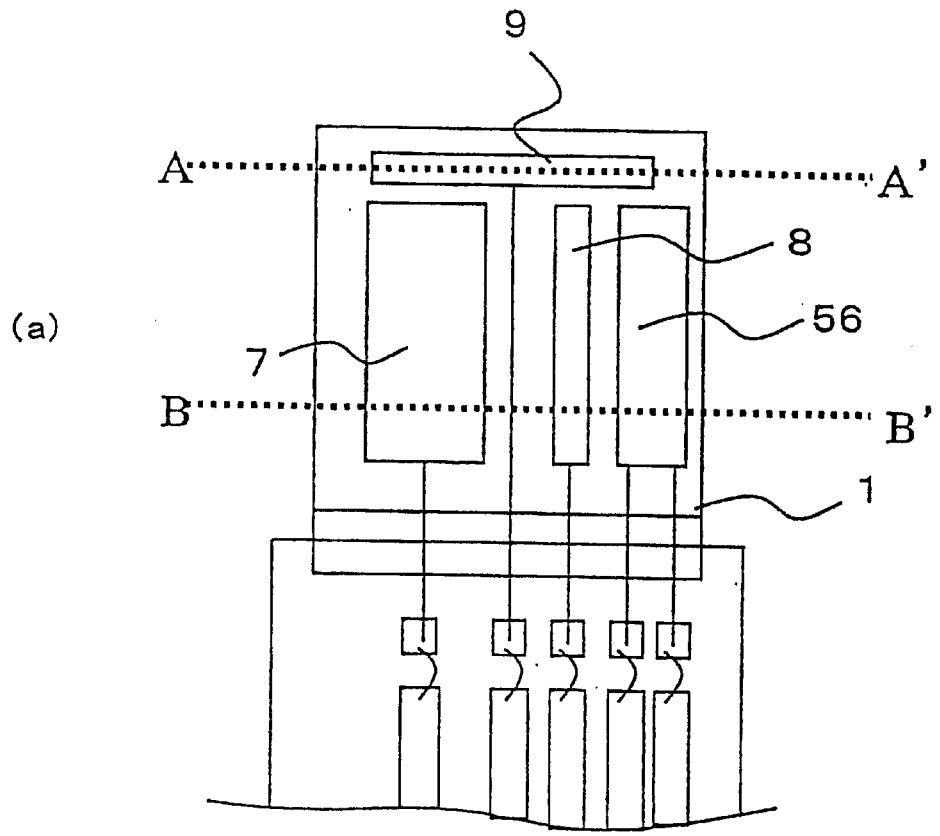
FIG. 15(a) shows a part of a sensor in a measuring apparatus according to this invention.
FIGS. 15(b) and (c) show cross-sections B–B' and A–A', respectively.
Figure 15:
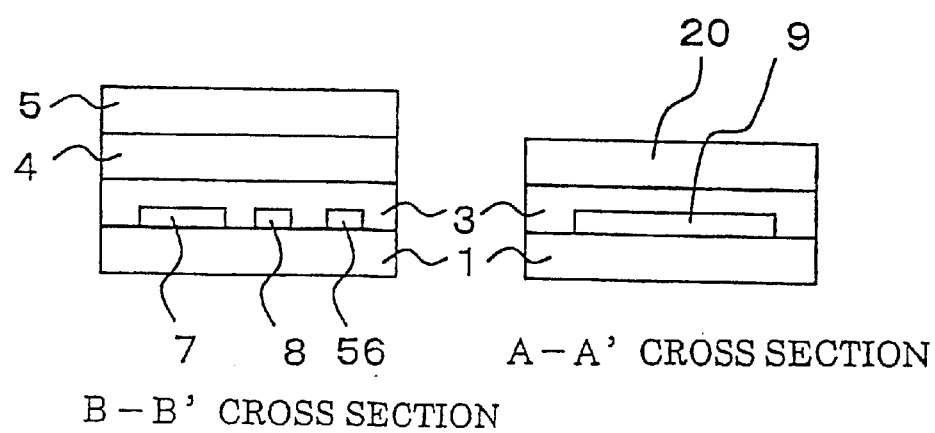
Figure 30:
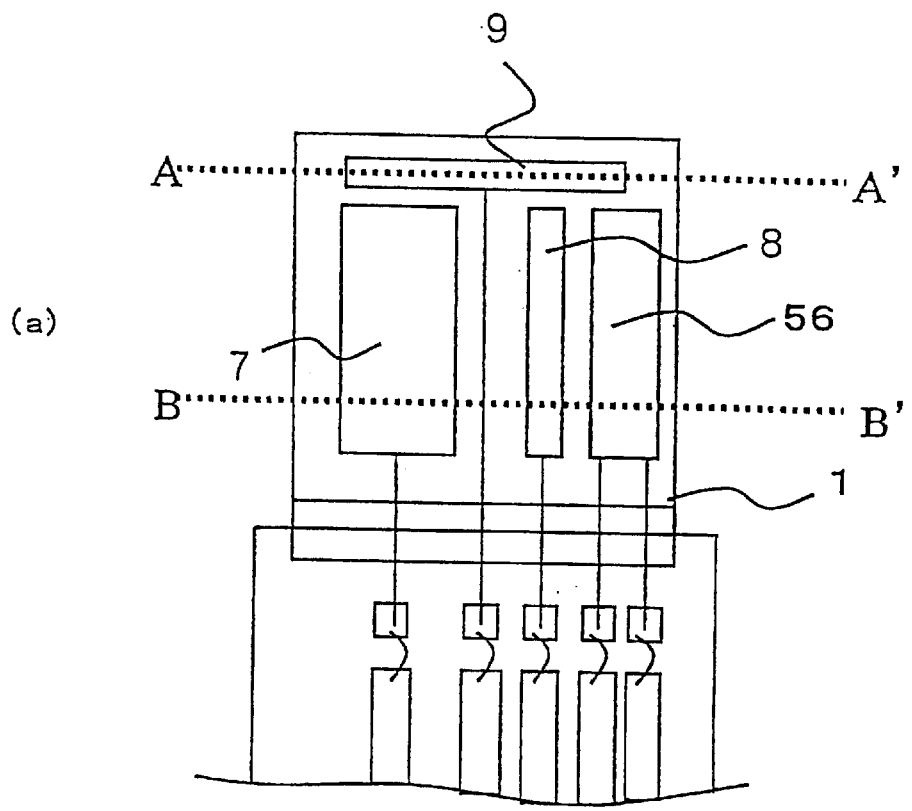
FIG. 30(a) is an example of a sensor in a measuring apparatus according to this invention.
FIGS. 30(b) and (c) show cross-sections B–B' and A–A', respectively.
Figure 30:
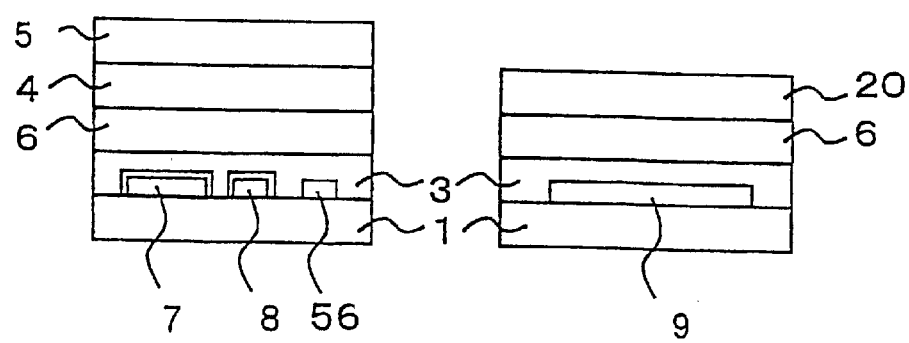

FIG. 30 and FIG. 15 show examples of a measuring apparatus in which a temperature sensor 56 is formed on a substrate comprising a biosensor. The measuring apparatus shown in FIG. 30 comprises a working electrode 7, a counter electrode 8, a reference electrode 9 and also a temperature sensor 56. On the working electrode 7, the counter electrode 8 and the temperature sensor 56 are sequentially formed a binding layer 3, an immobilized enzyme layer 4 and a permeation restricting layer 5. On the reference electrode 9 are formed a binder layer 3 and a protection layer 20. Such a configuration may allow a measured value to be accurately corrected on the basis of a temperature.

The pH sensor 57 is preferably, but not limited to, a glass electrode or ion-sensitive field effect transistor. The pH sensor 57 may be calibrated using a solution of a pH indicator in a calibration liquid for configuring the biosensor 50, for allowing calibration of the biosensor 50 and the pH sensor 57 at the same time. The pH indicator may be preferably an oxalate or phthalate solution which is used in a common glass pH meter.

The measuring apparatus of this embodiment may permit to accurately determine a level of a particular component in a sample in a wide temperature or pH range because a measured value from the enzyme electrode can be corrected using a temperature and a pH for each sample.

Although this embodiment has a configuration where the temperature sensor 56 and the pH sensor 57 are connected to the data processor 52, these may be connected to an electrochemical measuring circuit 51.

Embodiment 13

This embodiment relates to a measuring apparatus as shown in FIG. 33, further comprising a communication processor connected to a data processor, which transmits data from the data processor to an external device. It will be described with reference to FIG. 34.

Figure 34:
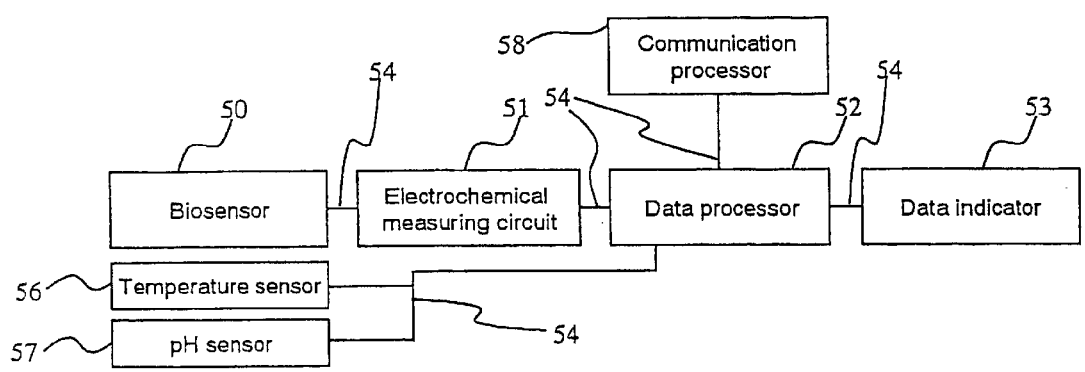
FIG. 34 shows another configuration example of a measuring apparatus according to this invention.

The measuring apparatus of this embodiment, as shown in FIG. 34, comprises a data processor 52 and a communication processor 58 which are mutually connected via a wiring 54. The communication processor 58 transmits information on a measured value to an external device. It is commonly a modem, but any device capable of communication processing may be used. A communication circuit used for communication may be, but not limited to, a telephone line, an infrared system or a wireless telephone. Information to be transmitted include those processed in the data processor 52 and those indicated by the data indicator 53. The communication processor 58 can transmit, for example, a current value in the biosensor 50, a password, a pH, a temperature, notes, a measured value calculated in the data processor 52, a timing for replacing the biosensor 50, a timing for calibration of the biosensor 50, data for checking operation or malfunction of the biosensor 50, an abnormal current and a signal from the electrochemical measuring circuit 51 processed by the operation unit of the data processor 52, to an external device such as a server or computer connected to the apparatus via a communication circuit. Information to be transmitted may be selected by setting as appropriate.

The measuring apparatus of this embodiment may be used to determine an urinary-sugar level in a patient with diabetes by him/herself at home, which may be then transmitted to a medical institute such as a hospital via a telephone line. It, therefore, may allow the patient to be appropriately advised in terms of diet or exercise control by the institute. Thus, it may allow administrating a patient with diabetes at home. Furthermore, since the apparatus can transmit data on malfunction of the enzyme electrode, services such as repair or maintenance of the apparatus from its manufacturer as appropriate.

Embodiment 14

This embodiment relates to a measuring apparatus as shown in FIG. 34 further comprising a printer 59, which will be described with reference to FIG. 35.

Figure 35:
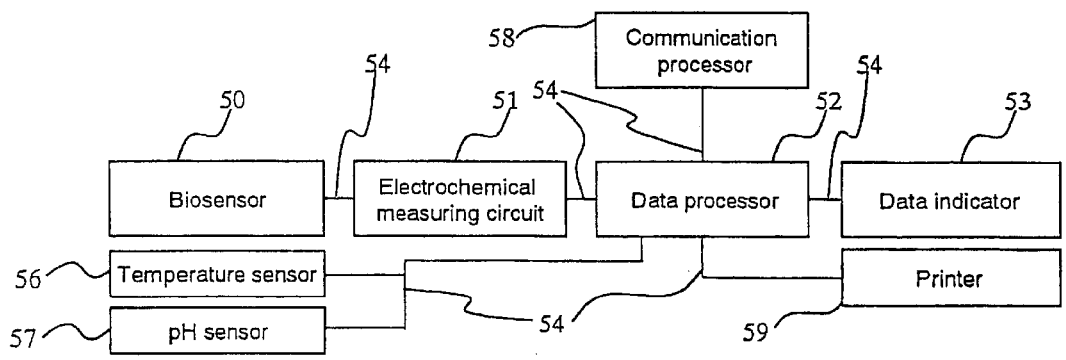
FIG. 35 shows another configuration example of a measuring apparatus according to this invention.

The measuring apparatus of this embodiment, as shown in FIG. 35, comprises a data processor 52 and a printer 59 which are mutually connected via a wiring 54. The printer 59 may be, but not limited to, a thermal, heat transfer, dot impact, inkjet or laser-beam dry printer, preferably a thermal printer which is of low cost and simple. The wiring 54 connecting the printer 59 to the data processor 52 may be an infrared ray, rather than an electric cord, taking an operation mode without a printer 59 into account. The printer 59 may be any printer which can print data to be indicated in the data indicator 53, but it may be set to print selected data.

The measuring apparatus of this embodiment allows data such as a measured value to be printed on a paper for storage, and also makes it possible that a patient with diabetes can use its printing function to print determination results on a paper, which the patient then brings to a physician for obtaining appropriate advice from the physician.

Embodiment 15

This embodiment relates to a measuring apparatus as shown in FIG. 35 further comprising an external storage 55, which will be described with reference to FIG. 36.

Figure 36:
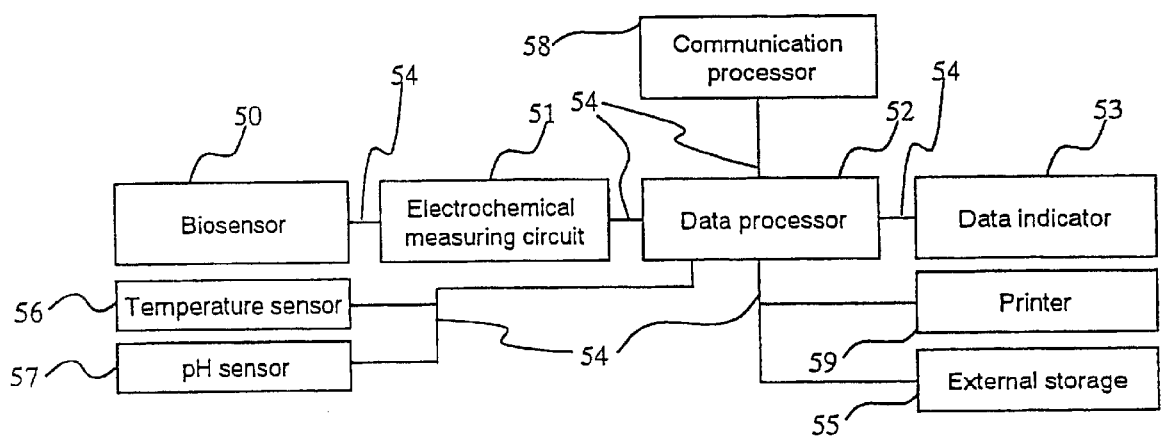
FIG. 36 shows another configuration example of a measuring apparatus according to this invention.

The measuring apparatus of this embodiment, as shown in FIG. 36, comprises a data processor 52 and an external storage which are mutually connected via a wiring 54. The external storage 55 may be a common storage medium; preferably magnetic storage media such as a floppy disk, semiconductor storage media such as a memory card, and optical storage media such as an optical disk because they are readily removed and inexpensive.

The measuring apparatus of this embodiment may be used to store measuring data on a storage medium, which a user can, as necessary, bring to a hospital. A physician in the hospital can analyze the stored measuring data to give an appropriate medical treatment to the patient with diabetes. Furthermore, a mass of measuring data can be stored for a long time. The apparatus is administered by means of passwords, so that patient's privacy can be protected and one apparatus may be used by two or more users. Data to be stored may be selected by setting as appropriate.

EXAMPLES

This invention will be specifically described with reference to Examples.

Example 1

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the overall surface was applied by spin coating a 1 v/v% solution of γ-aminopropyltriethoxysilane to form a binding layer, on which was applied by spin coating a 22.5 w/v% solution of albumin containing glutaraldehyde at 1 v/v%, to form an immobilized enzyme layer.

Then, the following two types of enzyme electrodes were manufactured, with different structures of the outermost layer (permeation restricting layer).

(1) On the overall surface of the immobilized enzyme layer was applied by spin coating and then dried a 0.3 wt % solution of a fluoroalcohol methacylate resin in perfluorohexane, to form a permeation restricting layer for providing the first enzyme electrode. Spin coating was conducted under the conditions of 3000 rpm and 30 sec. The fluoroalcohol methacrylate resin was Florard 722 (Sumitomo 3M), 1H,1H-perfluorooctyl polymethacrylate with an average molecular weight (Mn) of about 7000. Perfluorohexane as a diluent was Florard 726 (Sumitomo 3M). In addition, in a similar manner, on a quartz substrate was directly applied by spin coating a fluoroalcohol methacrylate resin to give a sample, whose thickness was then determined. After the film formation, a part of the film was removed with an ultrasonic cutter to provide a corrugated surface. Then, the corrugated surface was subject to observation with an atomic force microscope(AFM) to determine the film thickness. The thickness of the fluoroalcohol methacrylate was about 50 nm.

(2) On the overall surface of the immobilized enzyme layer was applied by spin coating and dried a 10 w/v% solution of a polyalkylsiloxane in toluene to form a permeation restricting layer for providing the second enzyme electrode. The polyalkylsiloxane was Pergan Z (Dow Corning).

Figure 5:
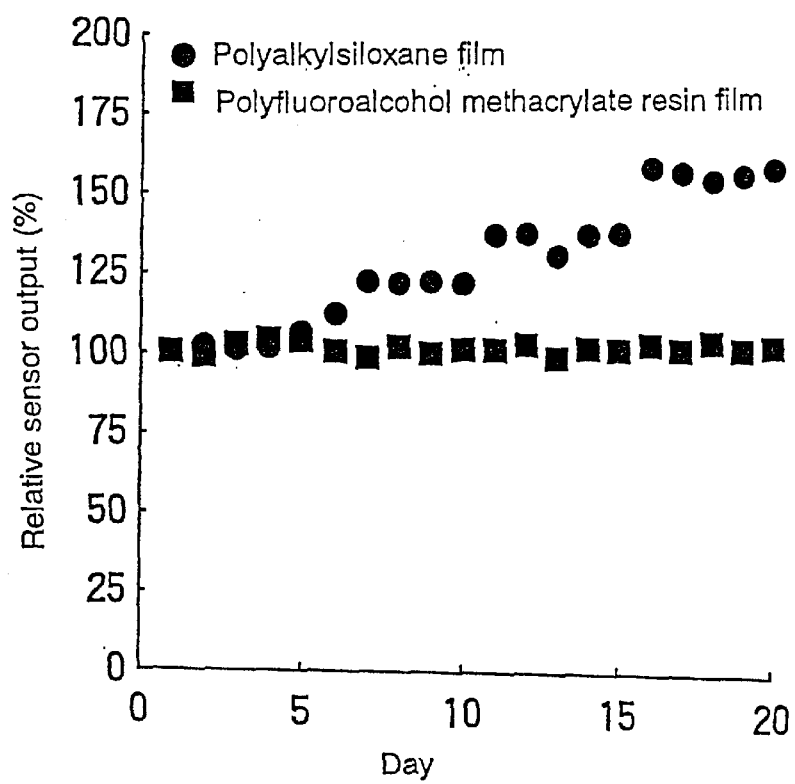
FIG. 5 shows stability of a glucose sensor according to this invention.

Two sensors comprising one of the first and the second enzyme electrodes thus manufactured were soaked for storing in a buffer solution of TES (Methyl N-tris (hydroxymethyl)-2-aminoethanesulfonate), pH 7, containing sodium chloride at 150 mM, while a 200 mg/dL standard solution of glucose was measured with these sensors once a day for 20 days. FIG. 5 shows outputs of these sensors for the glucose solution as relative values where the initial outputs were regarded as 100%. Table 1 shows comparison data on frequencies of cracks by observing the surface of the permeation restricting layer with a scanning electron microscope after a given period of use.

For the sensor comprising the polyalkylsiloxane, the sensor output has been increased from Day 7 (FIG. 5). Furthermore, in comparison with the initial state, there were observed cracks in the film, which were increased as the time elapsed (Table 1). In contrast, the sensor comprising the fluoroalcohol methacrylate resin gave stable outputs at least for 20 days, with no observed cracks.

TABLE 1

Cracks in a permeation restricting layer surface

| | Initial | Day 20 |
|---|---|---|
| Sensor comprising a fluoroalcohol methacrylate resin | | |
| Without an enzyme film | 1 | 1 |
| With an enzyme film | 1 | 1 |
| Sensor comprising a polyalkylsiloxane | | |
| Without an enzyme film | 2 | 3 |
| With an enzyme film | 2 | 5 |

Crack frequencies were categorized into five levels according to the number of cracks observed in an area of 1 cm×1 cm.

1: Not detectable
2: Low (several cracks)
3: Moderate (several tens of cracks or one large crack)
4: High (several hundreds of cracks or several large cracks)
5: Severe (several tens of large cracks)

The results in Table 1 indicate that increase of a relative sensor output might be due to cracks in the permeation restricting layer. The cracks in the permeation restricting layer probably generated because the layer could not endure expansion of the lower immobilized enzyme layer. The results in this example shows that a permeation restricting layer consisting of a fluoroalcohol methacrylate resin is adequately strong to endure expansion of the lower enzyme film.

Although this example has illustrated a sensor comprising a working electrode, a counter electrode and a reference electrode, on whose overall surface were formed a binding layer, an immobilized enzyme layer and a permeation restricting layer, these layers may be formed only on the working electrode.

Example 2

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the overall surface was applied by spin coating a 1 v/v% solution of y-aminopropyltriethoxysilane to form a binding layer, on which was applied by spin coating a 22.5 w/v% solution of albumin containing glutaraldehyde at 1 v/v%, to form an immobilized enzyme layer.

Then, on the immobilized enzyme layer was applied by spin coating and then dried a 0.3 wt % solution of a fluoroalcohol acrylate resin in hexafluoroxylene, to form a permeation restricting layer for providing the first enzyme electrode. Spin coating was conducted under the conditions of 3000 rpm and 30 sec. The applied solution was prepared by diluting a solution of 1H,1H,2H,2H-perfluorodecyl polyacrylate (acrylate resin/hexafluoroxylene=17/83, viscosity: 20 cps at 25° C.) with hexafluoroxylene to the indicated concentration.

The sensor comprising the enzyme electrode thus manufactured was soaked for storing in a buffer solution of TES (Methyl N-tris(hydroxymethyl)-2-aminoethanesulfonate), pH 7, containing sodium chloride at 150 mM, while a 200 mg/dL standard solution of glucose was measured with the sensor once a day for 20 days. The surface of the permeation restricting layer was observed with a scanning electron microscope for crack generation. The results showed that the sensor of this embodiment gave stable outputs at least for 20 days, with no observed cracks in the permeation restricting layer, as was in the sensor of Example 1 comprising a fluoroalcohol acrylate resin.

Example 3

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the overall surface was applied by spin coating a 1 v/v% solution of y-aminopropyltriethoxysilane to form a binding layer, on which was applied by spin coating a 5 w/v% solution of perfluorocarbon-sulfonate polymer, to form an ion-exchange polymer layer mainly consisting of the perfluorocarbon-sulfonate polymer (NAFION) and then applied by spin coating a 22.5 w/v% solution of albumin containing glutaraldehyde at 0.5 v/v% to form an immobilized enzyme layer.

On the surface was applied by spin coating a 0, 0.02, 0.06, 0.1 or 0.3 wt % of fluoroalcohol methacrylate resin at 3000 rpm for 30 sec.

The fluoroalcohol methacrylate resin was Florard 722 (Sumitomo 3M). The concentration of the stock solution of Florard 722 was 2 wt % when converted to the fluoroalcohol methacrylate resin. Perfluorohexane as a diluent was Florard 726 (Sumitomo 3M). The fluoroalcohol methacrylate resin was applied as a solution appropriately diluted with Florard 726.

From the results of relative outputs for each sensor as shown in FIG. 6, glucose-permeation restricting property was observed for a fluoroalcohol methacrylate resin concentration of 0.02 or higher wt %, 0.1 wt % allowed measurement in a wider range, and for 0.3 wt % or higher, current outputs were linear to a concentration of 3000 mg/dL which makes it possible to measure a higher concentration of glucose solution. An average response time for the sensor was below about 15 sec. Such a slow response was achieved because the permeation restricting layer could be formed as a very thin even film. Spin coating at 3000 rpm for 30 sec as was in this example may provide an even film about 0.01 μm to 0.1 μm of thickness.

Example 4

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the surface was applied by spin coating a 1 v/v% solution of y-aminopropyltriethoxysilane to form a binding layer, on which was applied by spin coating a 5 w/v% solution of perfluorocarbon-sulfonate polymer, to form an ion-exchange polymer layer mainly consisting of the perfluorocarbon-sulfonate polymer (NAFION) and then applied by spin coating a 22.5 w/v% solution of albumin containing glutaraldehyde at 1 v/v% to form an immobilized enzyme layer.

Then, two types of enzyme electrodes were manufactured, with different structures of the outermost layer.

For one enzyme electrode, on the surface of the immobilized enzyme layer was applied by spin coating and then dried a 0.3 wt % solution of a fluoroalcohol methacylate resin in perfluorohexane at 3000 rpm for 30 sec. The fluoroalcohol methacrylate resin was Florard 722 (Sumitomo 3M), whose average molecular weight (Mn) of about 7000. Perfluorohexane as a diluent was Florard 726 (Sumitomo 3M).

For the other enzyme electrode, on the surface of the immobilized enzyme layer was applied by spin coating and dried a 10 w/v% solution of a polyalkylsiloxane in toluene. The polyalkylsiloxane was Pergan Z (Dow Corning).

Figure 7:
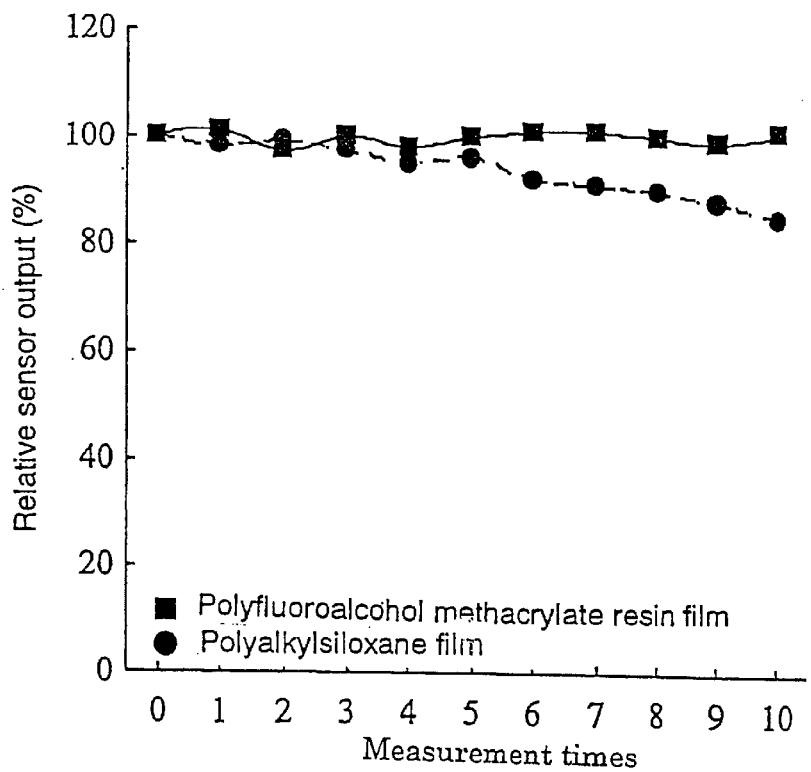
FIG. 7 shows stability of a glucose sensor according to this invention.

Two sensors comprising one of these enzyme electrodes thus manufactured were soaked for storing in a buffer solution of TES (Methyl N-tris(hydroxymethyl)-2-aminoethanesulfonate), pH 7, containing sodium chloride at 150 mM, while ten consecutive measurements were conducted for a 200 mg/dL standard solution of glucose containing urea at 400 mg/dL. FIG. 7 shows outputs of these sensors for the glucose solution as relative values where the initial outputs were regarded as 100%.

As a result, a sensor output was reduced from the second measurement to finally 86% in 10th measurement for the sensor comprising a polyalkylsiloxane while outputs were stable throughout 10 consecutive measurements for the sensor comprising a fluoroalcohol methacrylate resin. Such output stability in the sensor comprising a fluoroalcohol methacrylate resin can be explained by a lower surface free energy of the fluoroalcohol methacrylate resin than the polyalkylsiloxane, by which a reduced amount of urea is adhered.

Example 5

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the surface was applied by spin coating a 1 v/v% solution of y-aminopropyltriethoxysilane to form a binding layer, on which was applied by spin coating a 5 w/v% solution of perfluorocarbon-sulfonate polymer, to form an ion-exchange polymer layer mainly consisting of the perfluorocarbon-sulfonate polymer (NAFION) and then applied by spin coating a 22.5 w/v% solution of albumin containing glutaraldehyde at 1 v/v% to form an immobilized enzyme layer.

Then, two types of enzyme electrodes were manufactured, with different structures of the outermost layer.

For one enzyme electrode, on the surface of the immobilized enzyme layer was applied by spin coating and then dried a 0.3 wt % solution of a fluoroalcohol methacylate resin in perfluorohexane at 3000 rpm for 30 sec. The fluoroalcohol methacrylate resin was Florard 722 (Sumitomo 3M), whose average molecular weight (Mn) of about 7000. Perfluorohexane as a diluent was Florard 726 (Sumitomo 3M).

For the other enzyme electrode, on the surface of the immobilized enzyme layer was applied by spin coating and dried a 10 w/v% solution of a polyalkylsiloxane in toluene. The polyalkylsiloxane was Pergan Z (Dow Corning).

Figure 8:
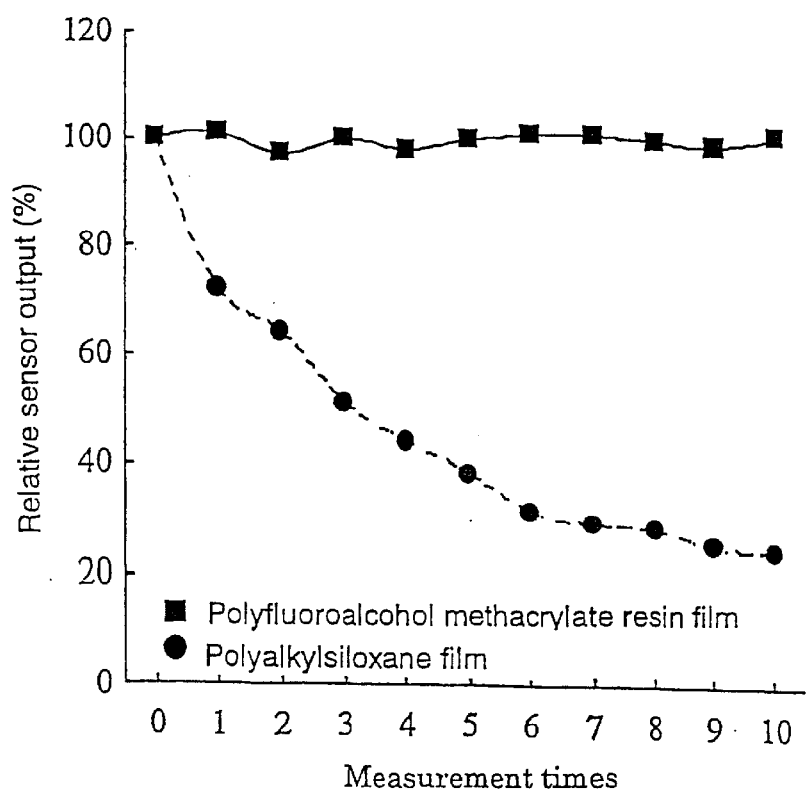
FIG. 8 shows stability of a glucose sensor according to this invention.
Figure 9:
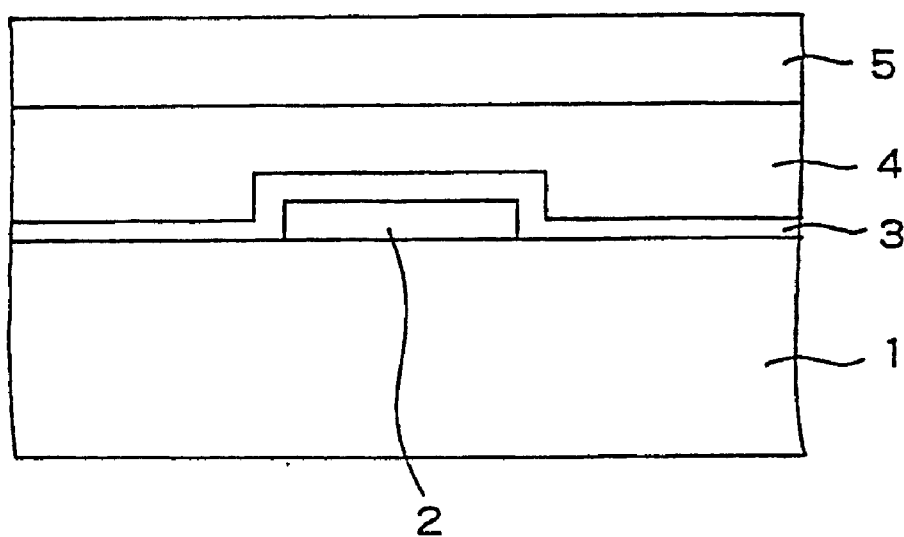
FIG. 9 is a cross section of a conventional enzyme electrode.

Two sensors comprising one of these enzyme electrodes thus manufactured were soaked for storing in a buffer solution of TES (Methyl N-tris(hydroxymethyl)-2- aminoethanesulfonate), pH 7, containing sodium chloride at 150 mM, while ten consecutive measurements were conducted for a normal urine control for quantification (Lifocheck; Biorad Ltd.) containing about 20 mg/dL glucose. FIG. 8 shows outputs of these sensors for the glucose solution as relative values where the initial outputs were regarded as 100%.

As a result, a sensor output was reduced from the second measurement to finally 28% in 10th measurement for the sensor comprising a polyalkylsiloxane while outputs were stable throughout 10 consecutive measurements for the sensor comprising a fluoroalcohol methacrylate resin. It indicates that the fluoroalcohol methacrylate resin can practically adequately minimize adhesion of materials causing sensor output reduction in urine.

Such output stability in the sensor comprising a fluoroalcohol methacrylate resin can be explained by a lower surface free energy of the fluoroalcohol methacrylate resin than the polyalkylsiloxane, by which the sensor does not react with interferent materials causing sensor output reduction such as urea.

Example 6

On a quartz substrate were formed a counter electrode, a reference electrode and three working electrodes (electrode area: 3 mm$^2$) Then, on the overall surface was applied by spin coating a 1 v/v% solution of γ-aminopropyltriethoxysilane. Then, on the three working electrodes were applied by spin coating a) a 22.5 w/v% solution of albumin containing glucose oxidase and glutaraldehyde at 1 v/v%, b) a 22.5 w/v% solution of albumin containing lactate oxidase and glutaraldehyde at 0.5 v/v% and c) a 22.5 w/v% solution of albumin containing ethanol oxidase and glutaraldehyde at 1 v/v%.

After thus forming an immobilized enzyme layer, two types of enzyme electrodes were manufactured, with different structures of the outermost layer.

For one enzyme electrode, on the surface of the immobilized enzyme layer was applied by spin coating and then dried a 0.3 wt % solution of a fluoroalcohol methacylate resin in perfluorohexane at 3000 rpm for 30 sec. The fluoroalcohol methacrylate resin was Florard 722 (Sumitomo 3M), whose average molecular weight (Mn) of about 7000. Perfluorohexane as a diluent was Florard 726 (Sumitomo 3M).

For the other enzyme electrode, on the immobilized enzyme layer was applied by spin coating and dried a 5 w/v% solution of a perfluorocarbon-sulfonate polymer to form an ion-exchange polymer layer mainly consisting of the perfluorocarbon-sulfonate polymer (NAFION).

Variation in measurement values was evaluated in repeated measurements using the sensors comprising an enzyme electrode. Specifically, 11 repeated measurements were conducted for a mixed solution containing 100 mg/dL glucose, 20 mM lactic acid and 20 mM ethanol to determine a coefficient of variation (CV value) for the measurement values. A coefficient of variation is a value represented by standard (deviation/average)X100.

The sensor comprising an enzyme electrode whose outermost layer consisted of a fluoroalcohol methacrylate gave stable measurement values irrespective of a measured component as shown in Table 2. It would be because the above resin layer does not have electric charge so that it little interacts with electrolytic substances such as lactic acid; the above resin layer is highly resistant to measured materials such as ethanol; or two or more working electrodes and two or more enzymes on the same insulating substrate does not mutually affect measurement for each target component.

On the other hand, for the enzyme electrode comprising the outermost layer of the perfluorocarbon- sulfonate polymer, the resin film is soluble to ethanol, so that its permeation-restricting property is lowered when measuring ethanol. In addition, the resin film has electric charge, which may cause a larger variation when measuring an electrolytic substance such as lactic acid.

TABLE 2

Evaluation of a coefficient of variation in measuring different components

| Component | Coefficient of variation (%) |
|---|---|
| Outermost layer of a fluoroalcohol methacylate resin | |
| Glucose | 3.1 |
| Lactic acid | 3.0 |
| Ethanol | 3.3 |
| Outermost layer of a perfluorocarbon-sulfonate polymer (NAFION) | |
| Glucose | 2.8 |
| Lactic acid | 6.7 |
| Ethanol | 72 |

Example 7

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$).

Then, on the overall surface was applied by spin coating a 1 v/v% solution of γ-aminopropyltriethoxysilane to form a binding layer, on which was applied by spin coating a 22.5 w/v% solution of albumin containing glutaraldehyde at 1 v/v%, to form an immobilized enzyme layer.

Then, the following two types of enzyme electrodes were manufactured, with different structures of the outermost layer.

(1) On the overall surface of the immobilized enzyme layer was applied by spin coating and then dried a 0.3 wt % solution of a fluoroalcohol methacylate resin in perfluorohexane, to form the first enzyme electrode. Spin coating was conducted under the conditions of 3000 rpm and 30 sec. The fluoroalcohol methacrylate resin was Florard 722 (Sumitomo 3M), 1H,1H-perfluorooctyl polymethacrylate with an average molecular weight (Mn) of about 7000. Perfluorohexane as a diluent was Florard 726 (Sumitomo 3M).

(2) On the overall surface of the immobilized enzyme layer was applied by spin coating and dried a 1.7 wt % solution of a copolymer of 1H,1H,2H,2H-perfluorodecyl polyacrylate and cyclohexyl methacrylate in hexafluoroxylene to form the second enzyme electrode, where the copolymerization ratio of 1H,1H,2H,2H-perfluorodecyl polyacrylate and cyclohexyl methacrylate was about 8:2, i.e., the ratio a/b was about 8/2 where "a" and "b" represent the numbers of 1H,1H,2H,2H-perfluorodecyl acrylate and cyclohexyl methacrylate moieties, respectively.

Two sensors comprising one of the first and the second enzyme electrodes thus manufactured were soaked for storing in a buffer solution of TES (Methyl N-tris (hydroxymethyl)-2-aminoethanesulfonate), pH 7, containing sodium chloride at 150 mM at 40° C. After 48 hours, 0 to 2000 mg/dL standard solutions of glucose were measured with these sensors. An applied voltage to the working electrode was 700 mV with reference to the reference electrode.

Figure 12:
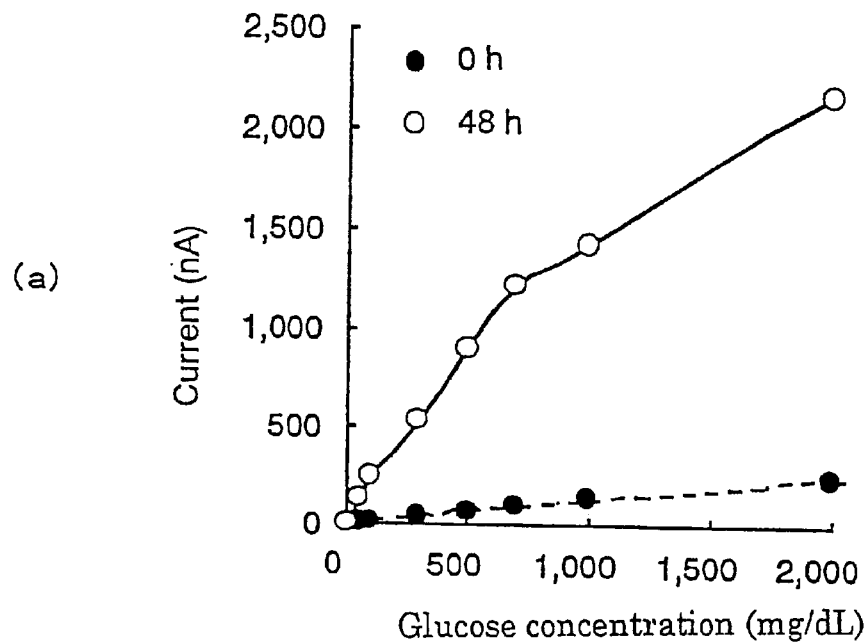
FIGS. 12(a) and 12(b) shows evaluation results for sensor output stability at 40° C. for a glucose sensor according to the first and second enzyme electrodes of Example 7, respectively, of this invention.
Figure 12:
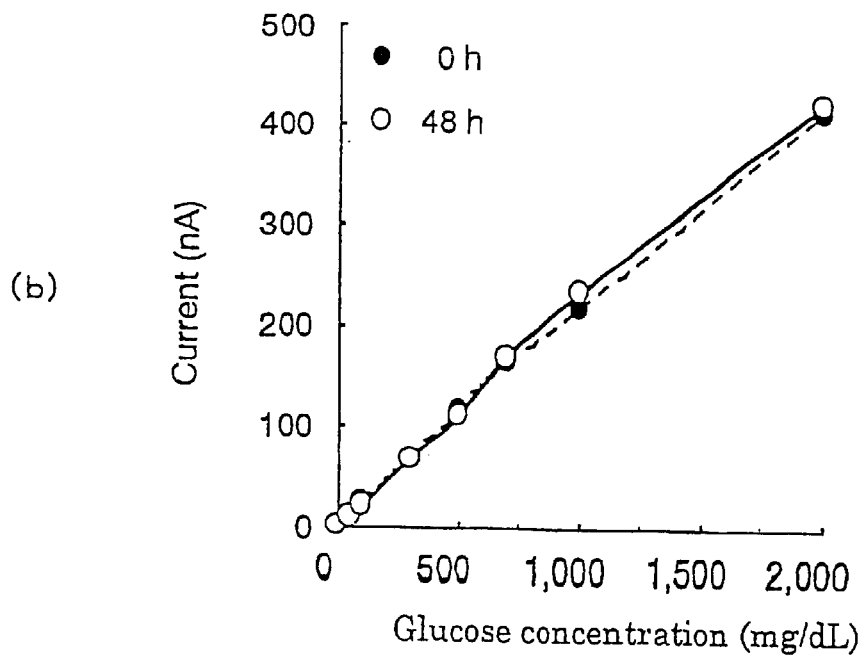

Thus, stability of a sensor output at 40° C. was tested. FIG. 12 shows measurement results for a sensor output before and 48 hours after soaking. FIGS. 12(*a*) and 12(*b*) show measurement results using the sensors comprising the first and the second enzyme electrodes, respectively. The sensor comprising the first enzyme electrode did not exhibit adequate stability while the sensor comprising the second enzyme electrode exhibited substantially the same outputs before (0 h in the figures) and 48 hours after soaking, showing excellent stability.

Example 8

On a 10 mm×6 mm quartz substrate were formed a working electrode of platinum (area: 7 mm$^2$), a counter electrode (area: 4 mm$^2$) and a reference electrode of silver/silver chloride (area: 1 mM$^2$).

Then, on the overall surface was applied by spin coating a 1 v/v% solution of γ-aminopropyltriethoxysilane to form a binding layer, on which was applied by spin coating a 22.5 w/v% solution of albumin containing glutaraldehyde at 1 v/v%, to form an immobilized enzyme layer.

Then, on the surface was applied by spin coating a solution of a) 85 wt % 1H,1H,2H,2H-perfluorodecyl polyacrylate and b) 0.085 wt % cyclohexyl polymethacrylate in hexafluoroxylene, to form the second enzyme electrode.

Figure 13:
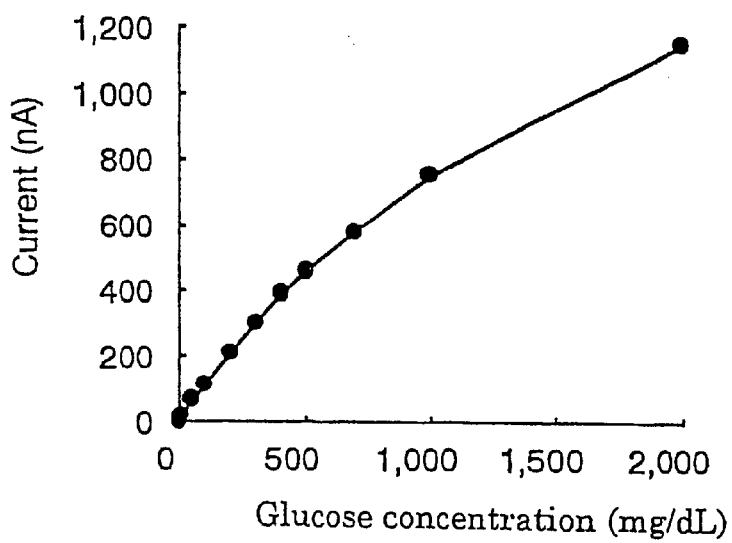
FIGS. 13(a) and 13(b) show measurement sensitivies of a glucose sensor according to this invention.
Figure 13:
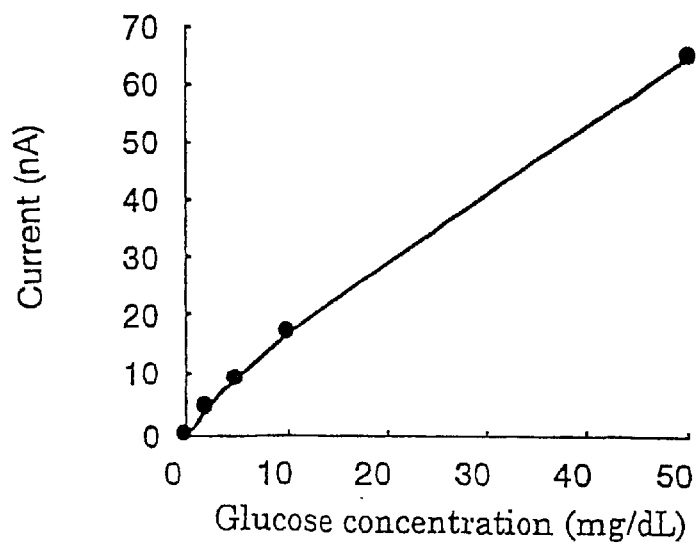

For the sensor comprising the enzyme electrode thus manufactured, calibration curves were obtained using 0 to 2000 mg/dL standard solutions of glucose. An applied voltage to the working electrode was 700 mV with reference to the reference electrode. The calibration curves are shown in FIGS. 13(*a*) and (*b*), which were obtained for the same sensor. As seen from these figures, the sensor of this example exhibited good sensitivity in a wide rage of 0 to 2000 mg/dL; in particular it gave an adequate current to glucose at 2 to 50 mg/dL. The sensor of this example may be, therefore, used to determine an urinary-sugar level for an individual whose urinary-sugar level is normal or a prediabetic individual, making it possible to collect data useful in prophylaxis for diabetes.

Figure 14:
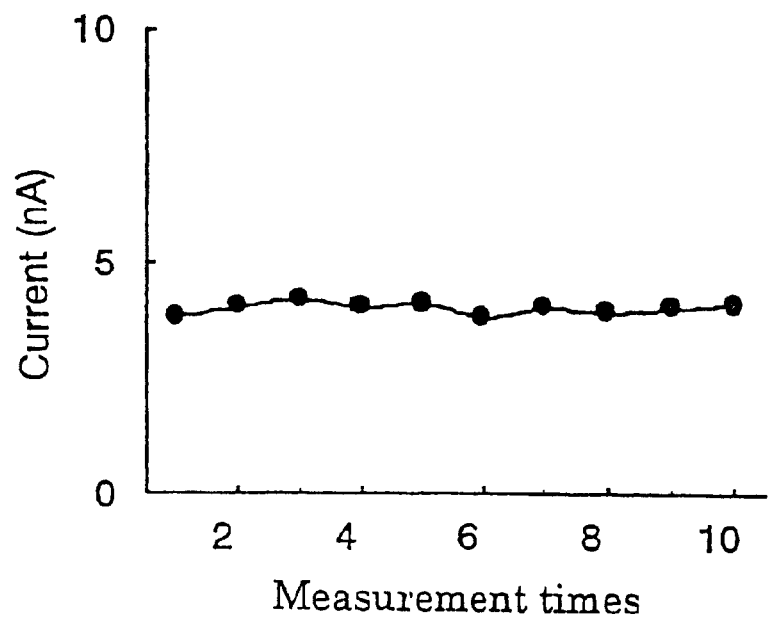
FIG. 14 shows stability of a glucose sensor according to this invention.

Ten consecutive measurements were conducted for an urine sample from a healthy individual containing glucose at about 2 mg/dL. The results are shown in FIG. 14. A reproductivity was about 3% and thus a lower level of glucose contained in urine could be determined with a good reproductivity.

Example 9

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 6M solution of urea containing sodium chloride at 150 mM, while a voltage of 0.7 V to the working electrode with reference to the reference electrode was applied for 10 min, to form an urea layer as an electrode protection layer on the working electrode. Formation of the urea layer was confirmed by observing infrared absorption spectra for a sample treated in a similar manner. Then, infrared absorption signals from urea were observed at 3440, 3340, 1640 and 1470 cm$^{-1}$. Since urea is more adhesive to platinum, the urea layer was selectively formed on the platinum electrode.

Then, on the surface was applied by spin coating a 1 v/v% solution of γ-aminopropyltriethoxysilane to form a binding layer, on which was applied by spin coating a 22.5 w/v% solution of albumin containing glutaraldehyde at 1 v/v%, to form an immobilized enzyme layer for providing an enzyme electrode.

As a control, an enzyme electrode was manufactured as described above except that an urea layer was not formed.

Figure 20:
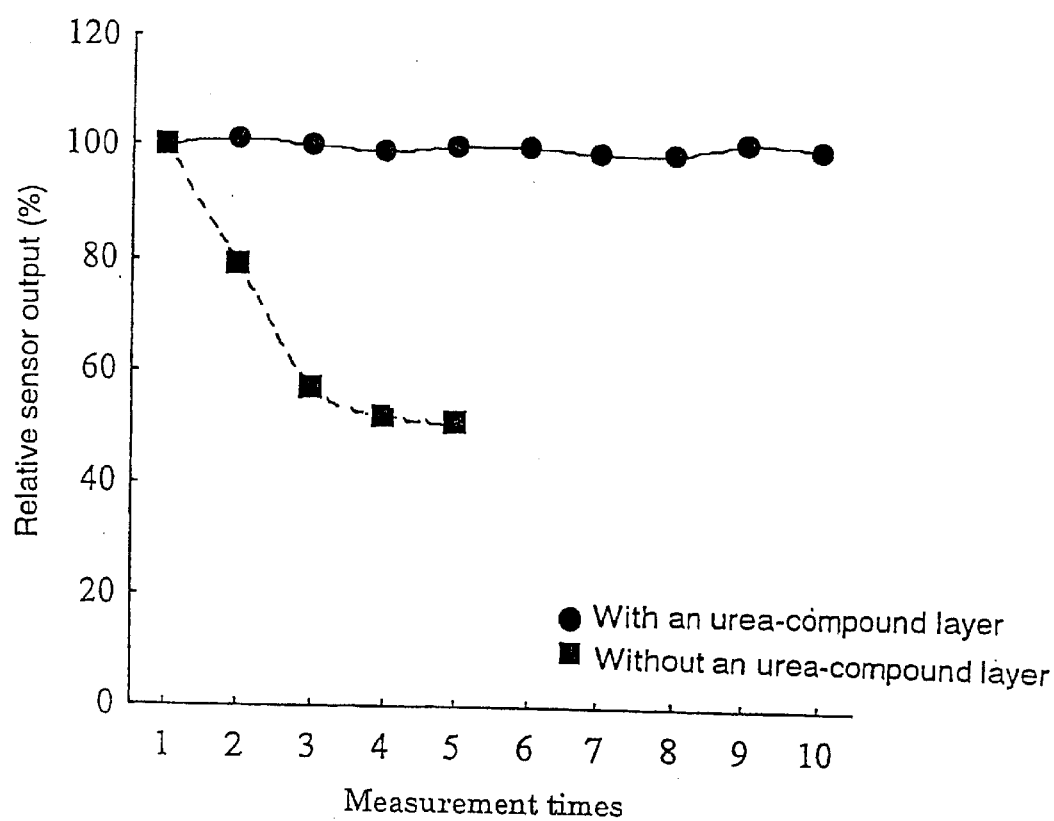
FIG. 20 shows stability of a biosensor according to this invention.

Two glucose sensors comprising one of these electrodes (detection unit) thus manufactured were soaked for storing in a buffer solution of TES (Methyl N-tris(hydroxymethyl)-2-aminoethanesulfonate), pH 7, containing sodium chloride at 150 mM, while five to ten consecutive measurements were conducted for a normal urine control for quantification (Lifocheck; Biorad Ltd.) containing about 20 mg/dL glucose. FIG. 20 shows outputs of these sensors for the glucose solution as relative values where the initial outputs were regarded as 100%.

As a result, a sensor output was sharply reduced from the second measurement to finally 52% in fourth measurement for the sensor without an urea layer while outputs were stable throughout 10 consecutive measurements for the sensor comprising an urea layer. The sensor comprising an urea layer gave such stable outputs because the film substantially completely restricted permeation of the contaminants in the normal urine control for quantification to the electrode.

Example 10

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 6M solution of urea containing sodium chloride at 150 mM, while a voltage of 0.7 V at the working electrode with reference to the reference electrode was applied for 10 min, to form an urea layer as an electrode protection layer on the working electrode.

Then, on the surface was applied by spin coating a 1 v/v% solution of γ-aminopropyltriethoxysilane to form a binding layer, on which was applied by spin coating a 5 w/v% solution of a perfluorocarbon-sulfonate polymer (NAFION), to form an ion-exchange polymer layer.

As a control, a binding layer and an ion-exchange layer were formed on the electrode as described above except that an urea layer was not formed.

Figure 21:
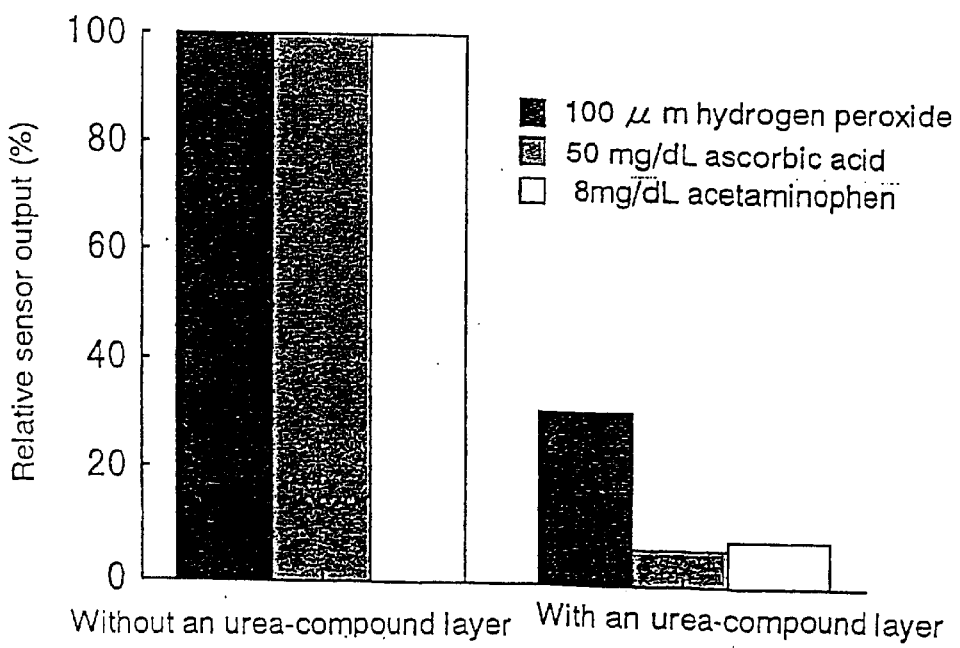
FIG. 21 shows a selective permeation property for a biosensor according to this invention.

Two glucose sensors comprising one of these electrodes (detection unit) thus manufactured were soaked for storing in a buffer solution of TES (Methyl N-tris(hydroxymethyl)-2-aminoethanesulfonate), pH 7, containing sodium chloride at 150 mM, while sensor outputs were determined for 100 μM hydrogen peroxide, 50 mg/dL ascorbic acid and 8 mg/dL acetaminophen. Outputs from the sensor with an urea layer are shown as relative values where an output from the sensor without an urea layer is regarded as 100% (FIG. 21).

It was consequently indicated that the urea layer formed on the surface of the working electrode restricted permeation of ascorbic acid and acetaminophen as interferent substances to improve selective permeability for hydrogen peroxide.

Example 11

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 6M solution of urea containing sodium chloride at 150 mM, while a voltage of 0.7 V at the working electrode with reference to the reference electrode was applied for 1, 3, 9 or 27 min, i.e., an urea layer was formed, varying a voltage application time.

Then, on the surface was applied by spin coating a 1 v/v% solution of γ-aminopropyltriethoxysilane to form a binding layer, on which was applied by spin coating a 5 w/v% solution of a perfluorocarbon-sulfonate polymer (NAFION), to form an ion-exchange polymer layer.

As a control, a binding layer and an ion-exchange layer were formed on the electrode as described above except that an urea layer was not formed.

Figure 22:
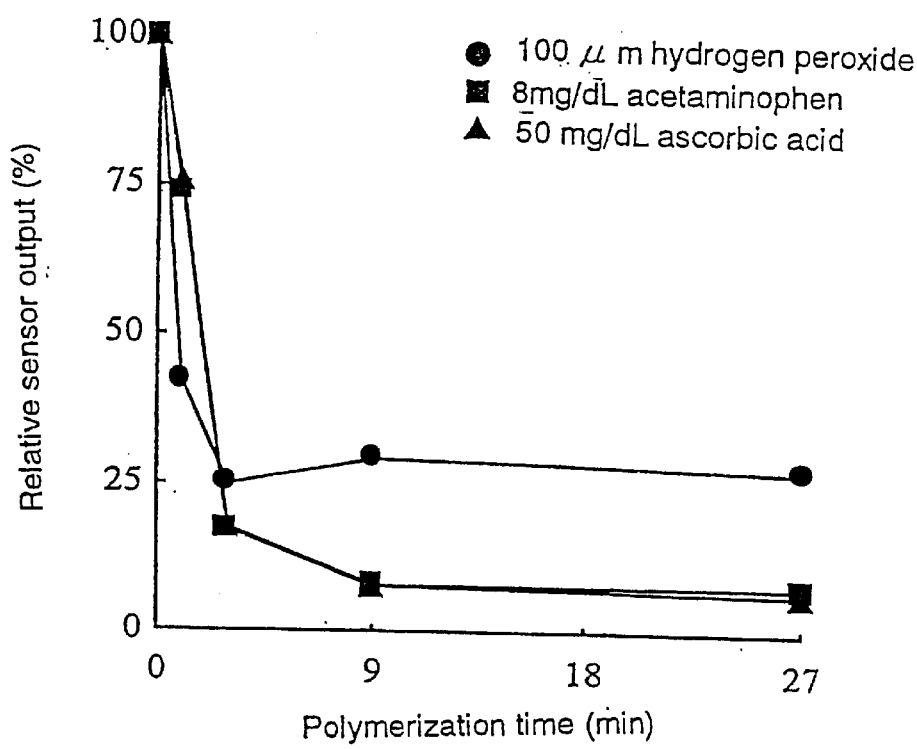
FIG. 22 shows a selective permeation property for a biosensor according to this invention.

Two glucose sensors comprising one of these electrodes (detection unit) thus manufactured were soaked for storing in a buffer solution of TES (Methyl N-tris(hydroxymethyl)-2-aminoethanesulfonate), pH 7, containing sodium chloride at 150 mM, while sensor outputs were determined for 100 $\mu$M hydrogen peroxide, 50 mg/dL ascorbic acid and 8 mg/dL acetaminophen. Output from each sensor with a given voltage application time are shown as relative values where an output from the sensor without an urea layer is regarded as 100% (FIG. 22).

It was consequently indicated that an urea layer formed on the sensor by applying the voltage for at least 3 min effectively restricted permeation of ascorbic acid and acetaminophen as interferent substances to improve selective permeability for hydrogen peroxide.

Example 12

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 0.1 mM, 0.1 M, 1 M or 6 M solution of urea containing sodium chloride at 150 nM, while a voltage of 700 mV at the working electrode with reference to the reference electrode was applied for 10 min.

Then, on the surface was applied by spin coating a 1 v/v% solution of γ-aminopropyltriethoxysilane to form a binding layer, on which was applied by spin coating a 5 w/v% solution of a perfluorocarbon-sulfonate polymer (NAFION), to form an ion-exchange polymer layer.

As a control, a binding layer and an ion-exchange layer were formed on the electrode as described above except that an urea layer was not formed.

Figure 23:
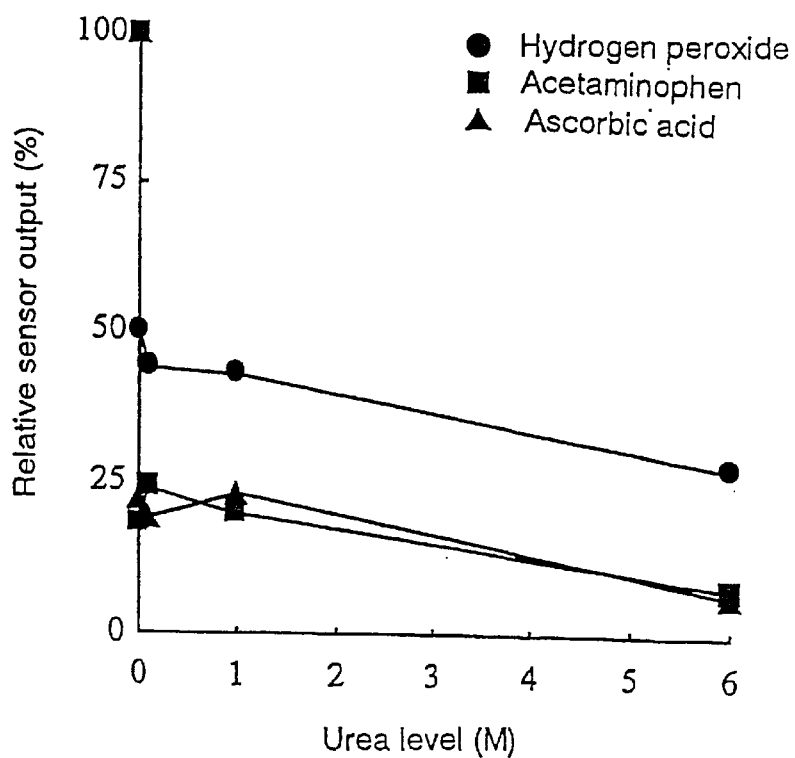
FIG. 23 shows a selective permeation property for a biosensor according to this invention.

Two glucose sensors comprising one of these electrodes (detection unit) thus manufactured were soaked for storing in a buffer s olution of TES (Methyl N- tris(hydroxymethyl)-2-aminoethanesulfonate), pH 7, containing sodium chloride at 150 mM, while sensor outputs were determined for 100 $\mu$M hydrogen peroxide, 50 mg/dL ascorbic acid and 8 mg/dL acetaminophen. Output from each sensor with a given voltage application time are shown as relative values where an output from the sensor without an urea layer is regarded as 100% (FIG. 23).

It was consequently indicated that treating the electrode with at least 0.1 mM urea solution at an applied voltage of 700 mV for 10 min provided good selectivity for hydrogen peroxide.

Example 13

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 6M solution of urea containing sodium chloride at 150 mM, while a voltage of 0.7 V to the working electrode with reference to the reference electrode was applied for 10 min, to form an urea layer on the working electrode. Formation of the urea layer was confirmed by observing infrared absorption spectra for a sample treated in a similar manner.

Then, on the surface was applied by spin coating a 1 v/v% solution of γ-aminopropyltriethoxysilane to form a binding layer, on which were sequentially applied by spin coating a 5 w/v% solution of a perfluorocarbon-sulfonate polymer (NAFION) to form an ion-exchange polymer layer; a 22.5 w/v% solution of albumin containing glucose oxidase and glutaraldehyde at 1 v/v%, to form an immobilized enzyme layer; and a 0.3 wt % solution of a polyfluoroalcohol methacrylate resin in perfluorohexane to form a permeation restricting layer, for providing an enzyme electrode.

As a control, an enzyme electrode was manufactured as described above except that an urea layer was not formed.

Figure 24:
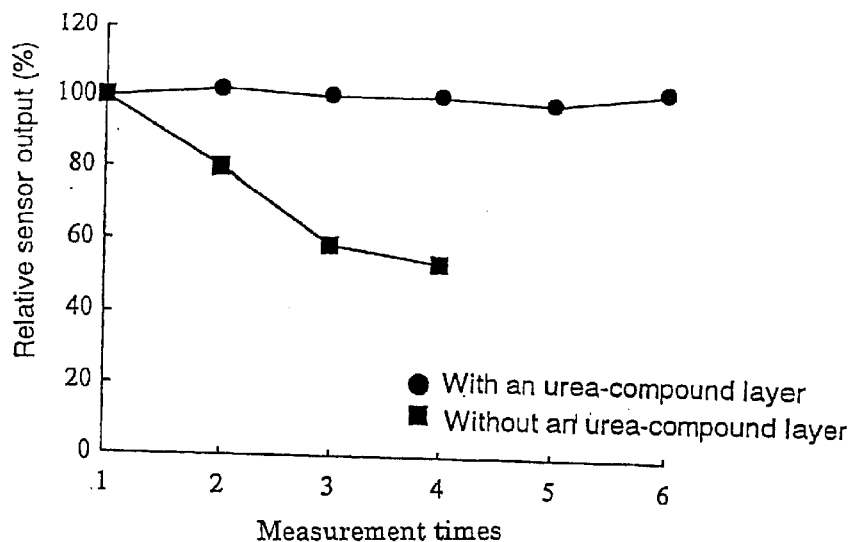
FIG. 24 shows stability of a biosensor according to this invention.

Two glucose sensors comprising one of these electrodes (detection unit) thus manufactured were soaked for storing in a buffer solution of TES (Methyl N-tris(hydroxymethyl)-2-aminoethanesulfonate), pH 7, containing sodium chloride at 150 mM, while four to six consecutive measurements were conducted for an abnormal urine control for quantification (Lifocheck; Biorad Ltd.) containing about 302 mg/dL glucose. FIG. 24 shows outputs of these sensors for the glucose solution as relative values where the initial outputs were regarded as 100%.

As a result, a sensor output was gradually reduced from the second measurement to finally 53% in fourth measurement for the sensor without an urea layer while outputs were stable throughout 6 consecutive measurements for the sensor comprising an urea layer. The sensor comprising an urea layer gave such stable outputs because the film substantially completely restricted permeation of the contaminants in the abnormal urine control for quantification to the electrode.

Example 14

On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). The substrate was soaked in a 6M solution of urea containing sodium chloride at 150 mM, while a voltage of 0.7 V to the working electrode with reference to the reference electrode was applied for 10 min, to form an urea layer on the working electrode.

Then, on the surface was applied by spin coating a 1 v/v% solution of γ-aminopropyltriethoxysilane to form a binding layer, on which were applied by spin coating a 5 w/v% solution of a perfluorocarbon-sulfonate polymer (NAFION) to form an ion-exchange polymer layer for providing a detection unit of a sensor.

As a control, on a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). On the surface were sequentially applied by spin coating a 1 v/v% solution of γ-aminopropyltriethoxysilane, a 2 w/v% solution of acetylcellulose ad a 5 w/v% solution of a perfluorocarbon-sulfonate polymer (NAFION), to form an electrode unit of a sensor.

Figure 25A:
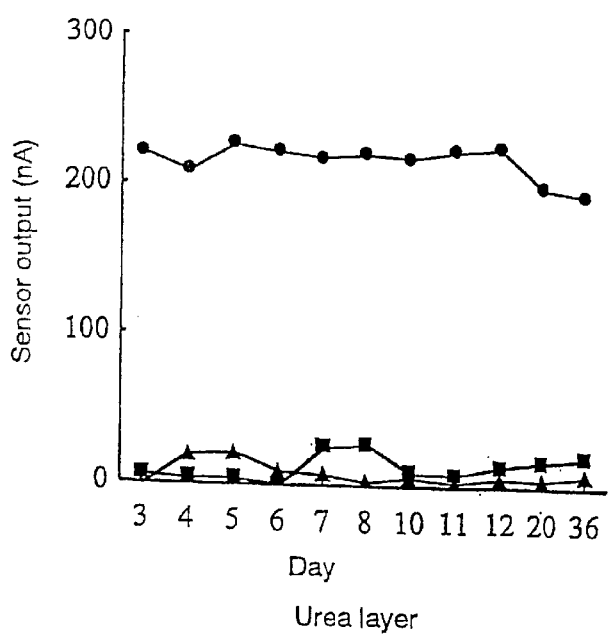
FIGS. 25(a) and (b) shows stability of a biosensor according to this invention.
Figure 25B:
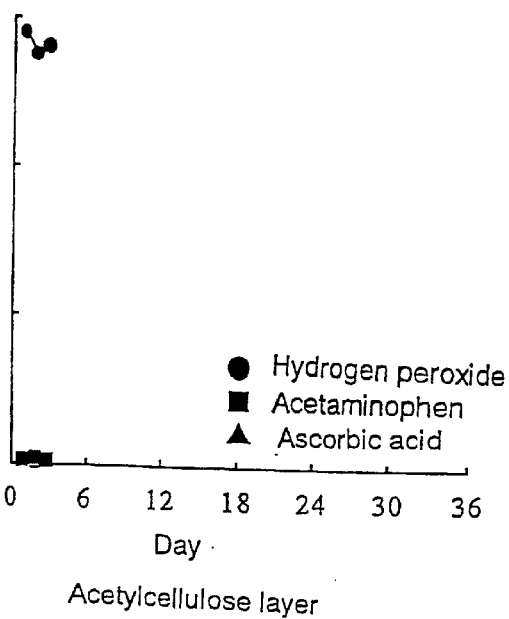
Figure 26:
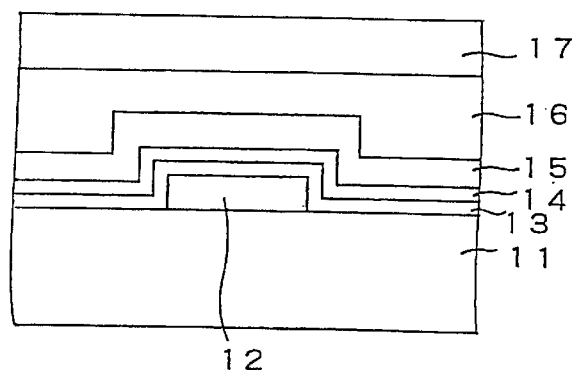
FIG. 26 is a cross section of a conventional enzyme electrode.
Figure 27:
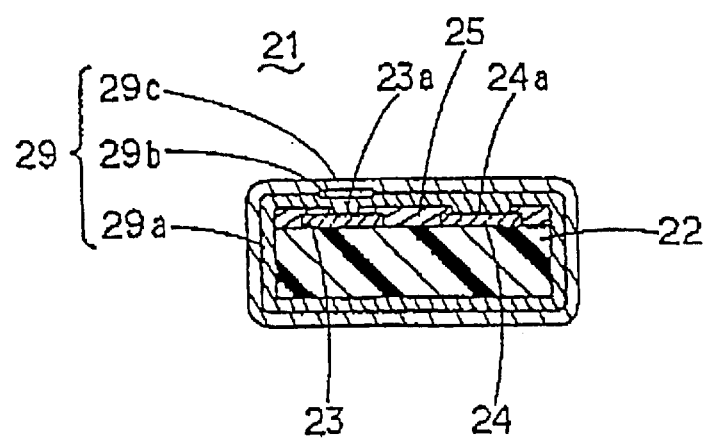
FIG. 27 is a cross section of a conventional enzyme electrode.

Two glucose sensors comprising one of these electrodes (detection unit) thus manufactured were soaked for storing in a buffer solution of TES (Methyl N-tris(hydroxymethyl)-2-aminoethanesulfonate), pH 7, containing sodium chloride at 150 mM, while sensor outputs were determined for 100 $\mu$M hydrogen peroxide, 50 mg/dL ascorbic acid and 8 mg/dL acetaminophen (FIG. 25).

Consequently, the sensor comprising an urea layer could selectively measure hydrogen peroxide at least 36 consecutive days, while the sensor comprising the acetylcellulose layer could measure it only for 3 days and subsequent measurements could not be conducted due to failure of the sensor. The acetylcellulose layer could not be formed as an even film, so that the layer was detached during operation, resulting in the failure of the sensor itself.

Example 15

This example relates to an example of a measuring apparatus having the configuration shown in FIG. 31.

First, there will be described a procedure for manufacturing a biosensor unit in the measuring apparatus of this example. On a 10 mm×6 mm quartz substrate were formed a working electrode of platinum (area: 7 mm$^2$), a counter electrode (area: 4 mm$^2$) and a reference electrode of silver/silver chloride (area: 1 mm$^2$). Then, on the overall surface were sequentially applied by spin coating a 1 v/v% solution of y-aminopropyltriethoxysilane to form a binding layer; a 22.5 w/v% solution of albumin containing 56.5 U/µL glucose oxidase and 1 v/v% glutaraldehyde to form an immobilized enzyme layer; and a 1.7 wt % solution of a polyfluoroalcohol acrylate resin to form a permeation restricting layer. The polyfluoroalcohol acrylate resin was 1H,1H,2H,2H-perfluorodecyl polyacrylate. The diluent was hexafluoroxylene. The conditions of spin coating were 3000 rpm and 30 sec.

Using a biosensor comprising an electrode unit thus manufactured, a measuring apparatus having a configuration shown in FIG. 31 was manufactured, where the electrode unit was connected, via wire bonding, with a flexible substrate, which was connected with an electrochemical measuring circuit via a pin-jack type wiring.

The electrochemical measuring circuit was a potentiostat, HOKUTODENKOPOTENTIOSTAT/GALVANOSTATHA150G (Hokuto Denko). The data processor was a personal computer, PC-9821RaII23 (NEC corporation). The data indicator 53 was a display, PC-KP531 (NEC corporation). The electrochemical measuring circuit, the data processor and the data indicator 53 were mutually connected via a pin-jack type wiring.

Operation of the measuring apparatus of this example will be described.

An operator soaked the biosensor comprising an enzyme electrode into a buffer of 1 mM TES (Methyl N-tris(hydroxymethyl)-2-aminoethanesulfonate), pH 7, containing sodium chloride at 150 mM, and turned the apparatus on. Then, the data indicator displayed a message "Time setting; Enter a current time". According to the indication, the operator entered the current time by key operation, and then the data indicator displayed the message "A current time was entered". When an entered time was incorrect, the message "Time setting; Enter a current time" is displayed. Thus, the entered current time is stored in the data processor.

Then, the data indicator displayed a message "Standby mode. Please wait.". After a current from the enzyme electrode, the data indicator displayed a message "Calibration; Soak the electrode into a calibration solution". According to the indication, the operator soaked the biosensor into a calibration solution of 200 mg/dL glucose for calibration. Then, the data indicator displayed a message "Calibration was normally finished. After washing, resoak the electrode into the buffer.". Whether the calibration has been normally conducted is judged by the data processor and the result is displayed on the data indicator. If the calibration is not normally conducted, a message "Not calibrated. After washing the electrode, resoak it into the calibration solution" or "The electrode is broken. Replace it." is displayed. After the calibration, the operator soaked the enzyme electrode into the buffer for measurement. When the electrode is not returned into the buffer 10 sec after the calibration is completed, an alarm sounds.

Then, the operator selected the item "Start measurement" displayed on the data indicator, and then the indicator displayed a message "Measurement will be started. Soak the electrode into an urine sample.". According the indication, the operator soaked the electrode into an urine sample to initiate measurement. Ten seconds after the measurement initiation, the data indicator displayed a message "Measurement has been normally finished. An urinary-sugar level is ... mg/dL.". Whether the measurement has been normally conducted is judged by the data processor and the result is displayed on the data indicator. If the measurement is not normally conducted, a message "Not measured. After washing the electrode, resoak it into the urine solution" or "The electrode is broken. Replace it." is displayed.

After the measurement, the data indicator displayed a message "Wash and resoak the electrode into the buffer". When the electrode is not returned into the buffer 10 sec after the measurement is completed, an alarm sounds. Then, the operator selected the item "Completion of measurement" on the data indicator, to complete the measurement.

For the measuring apparatus of this example, a measuring time may be set in advance. At the set time, an indicating sound generates while the data indicator displays a message "Measurement will be started. Soak the electrode into an urine sample.". The time may be set as appropriate and a plurality of times may be set.

After entering data in the data processor in the measuring apparatus of this invention, an indicating sound is generated in either case that the entry is acceptable or unacceptable. An indicating light rather than an indicating sound may be employed. When an abnormal current is detected between the enzyme electrode, the electrochemical measuring circuit, the data processor and the wiring, an abnormal-current indicator displays a message "lAn abnormal current was detected" on the data indicator. Displaying the message may prevent failure of the apparatus.

Since all of the biosensor, the electrochemical measuring circuit and the data processor are connected via a pin-jack type wiring, they are readily removed and may be replaced as necessary.

As described above, the measuring apparatus of this example may be used to regularly conduct measurement at a given time without misoperation and anyone can easily operate it.

Example 16

This example relates to an example of a measuring apparatus having a configuration shown in FIG. 33. The measuring apparatus is the apparatus as described in Example 15 further comprising a pH sensor and a temperature sensor.

The temperature sensor was a thermocouple type and the pH sensor was an ion-sensitive field effect transistor type. The pH sensor, the temperature sensor, the electrochemical measuring circuit, the data processor and the data indicator were mutually connected via an electric wire.

Operation of the measuring apparatus of this example will be described.

An operator soaked the enzyme electrode into a buffer of 1 nM TES (Methyl N-tris(hydroxymethyl)-2-aminoethanesulfonate), pH 7, containing sodium chloride at 150 mM, and turned the apparatus on. After 1 min, the base current of the enzyme electrode became stable. In this state, the enzyme electrode was soaked into a 200 mg/dL standard solution of glucose for calibration. Since the glucose standard solution contains a pH indicator, the pH sensor can be calibrated at the same time. Except replacement of the electrode, the apparatus may be kept power-ON as long as the enzyme electrode is connected.

Then, the operator selected the item "Start measurement", and the data indicator displayed a message "Measurement will be started. Soak the electrode into an urine sample.".

According the indication, the operator sequentially measured an urinary-sugar level for samples from two diabetic subjects once per a sample. During the measurement, a memo registration means was used to enter a blood pressure and a temperature at the same time for each subject. Then, 10 sec. after the first subject soaked the electrode into urine, the data indicator displayed a message "Measurement has been normally finished. An urinary-sugar level is 80 mg/dL." and a voice message "Measurement has been normally finished. An urinary-sugar level is 80 mg/dL." sounded. After 20 sec, the second subject soaked the enzyme electrode into urine. After 10 sec, the data indicator displayed a message "Measurement has been normally finished. An urinary-sugar level is 180 mg/dL." and a voice message "Measurement has been normally finished. An urinary-sugar level is 180 mg/dL." sounded. These results were compared with those obtained from an existing laboratory apparatus (Hitachi Automatic Analyzer 7050 according to a glucose dehydrogenase technique). There were good matching and a higher correlation between the measurements.

Thus, the measuring apparatus of this example may be used to sequentially detect an urinary-sugar level for two subjects. Even a subject with a weak eyesight could reliably determine his/her urinary-sugar level. In addition, the memo-registration means could be used to access a temperature and a blood pressure entered in advance. It allowed an operator to compare these values to the urinary-sugar level for carefully administrating subject's conditions. Furthermore, the measured values were corrected for a temperature and a pH, so that highly precise detection comparable to an existing laboratory apparatus could be conducted.

Example 17

This example relates to an example of a measuring apparatus having a configuration shown in FIG. 34. This measuring apparatus is the apparatus in Example 16 further comprising a communication processor 58.

The communication processor 58 was a modem-terminal adapter, PC-IT65S1P (NEC corporation). The pH sensor, the temperature sensor, the electrochemical measuring circuit, the data processor, the data indicator and the communication processor were mutually connected via an electric wire.

This apparatus was used to detect an urinary-sugar level for one diabetic twice (2 hours after breakfast and dinner) a day for 30 days. A measured value was sent to a hospital via a telephone line one by one.

Thus, the patient successfully observed the measuring times, so that the hospital could plot the received data into a graph and analyze it for appropriately administrating the patient's conditions.

Example 18

This example relates to an example of a measuring apparatus having a configuration shown in FIG. 35. The measuring apparatus is the apparatus in Example 17 further comprising a printer 59. The printer 59 was a laser printer, Multiwriter 2000X (NEC corporation). The printer was connected with the data processor via a printer cable, PC-CA202. There will be described measurement results using the measuring apparatus of this example.

This apparatus was used to detect an urinary-sugar level for consecutive 100 diabetics. The apparatus was calibrated only once when starting it. For the same samples, an urinary-sugar level was detected with an existing laboratory apparatus (Hitachi Automatic Analyzer 7050 according to a glucose dehydrogenase technique), whose results were compared with those from the measuring apparatus of this example. Then, a coefficient of correlation obtained was 0.96 and a regression formula was Y=1.09X+88. It-was shown that the apparatus of this example could conduct detection with a precision comparable to that in the existing laboratory apparatus. A measuring time for the apparatus of this example was as short as about 90 sec per a sample, allowing an operator to quickly conduct detection. Furthermore, the apparatus of this example was equipped with the printer 59, so that the measurement results could be quickly printed for confirmation. The patient could show a physician the printed results in a hospital for receiving his/her advice.

Example 19

This example relates to an example of a measuring apparatus having a configuration shown in FIG. 36. The measuring apparatus is the apparatus as described in Example 18 further comprising an external storage 55. The external storage was a 3.5 inch optical disk unit, PC-OD302R (NEC corporation). The external storage was connected with the data processor via an electric wire. Operation of the measuring apparatus of this example will be described.

An operator soaked the enzyme electrode into a buffer of 1 mM TES (Methyl N-tris(hydroxymethyl)-2-aminoethanesulfonate), pH 7, containing sodium chloride at 150 mM, and turned the apparatus on. After about 1 min, the base current of the enzyme electrode became stable. In this state, the enzyme electrode was soaked into a 200 mg/dL standard solution of glucose for calibration and the enzyme electrode was calibrated.

Then, the operator selected an item "Entry of the number of subjects" displayed on the data indicator, and a message "Enter the number of subjects" was displayed. After the operator entered the number of subjects according to this instruction, the data indicator displayed a message ". . . subjects will be tested. (Yes, Y/No. N)". "Yes, Y" was selected and then a message ". . . subjects can be tested" was displayed. If "No, N" is selected, the message "Enter the number of subjects" is again displayed and the above procedure is repeated until "Yes, Y" is selected.

The operator selected an item "Password" on the data indicator and then "Registration of a password". The data processor recognizes that the password entering button has been pushed to make the data indicator display a message "A password will be registered. Enter a 4 digit number.". After the operator entered a 4 digit number according to this instruction, the data indicator displayed a message "Enter the same password". After the operator entered the same number again, a message "The password was received" was displayed. Passwords are registered by the number of subjects. Thus, the registered passwords are stored in the memory in the data processor.

Then, the data indicator displayed a message "Measurement will be started. After entering the password, soak the electrode into an urine sample.". According to this instruction, the operator entered the password and soak the electrode into urine to start detection. Then, the data indicator displayed a message "Measurement has been normally finished. An urinary-sugar level is . . . mg/dL.". If the measurement is not normally conducted, a message "Not measured. After washing the electrode, resoak it into the urine solution" or "The electrode is broken. Replace it." is displayed. If a correct password is not entered, the message "Measurement will be started. After entering the password, soak the electrode into an urine sample." is again displayed. If an incorrect password is entered three consecutive times, all the measured data are deleted and the setting returns to the initial state.

After normally completing detection, the data indicator displayed a message "Wash and resoak the electrode into the buffer".

The operator selected "Memo registration" on the data indicator and then a message "A memo is registered? (Yes, Y/No, N)" was displayed. After selecting "Y", a message "Enter the password" was displayed. The operator entered the password and memo data, and then the data indicator displayed the message "A memo is registered? (Yes, Y/No, N)". The operator selected "Y" and entered the memo data, and then the data indicator again displayed the message "A memo is registered? (Yes, Y/No, N)". The operator selected "Y" and registered the memo. For stopping the input process, "N" is selected. When reading, amending or deleting a registered memo, a message "After entering the password, designate the memo number." is displayed. According to the instruction, the operator can enter the password to read, amend or delete the memo. If an incorrect password is entered, a message "The password is incorrect. Enter the password again." is displayed. If an incorrect password is entered three consecutive times, all the memo data are deleted and the setting returns to the initial state.

Measurement results obtained using the measuring apparatus of this example will be described. The apparatus of this example was used to repeatedly measure an urinary-sugar level for two diabetics twice a day for a week. The apparatus was calibrated only once when starting it. For the same samples, an urinary-sugar level was detected with an existing laboratory apparatus (Hitachi Automatic Analyzer 7050 according to a glucose dehydrogenase technique), whose results were compared with those from the measuring apparatus of this example. Then, a coefficient of correlation obtained was 0.955 (n=28). It was shown that the apparatus of this example could conduct detection with a precision comparable to that in the existing laboratory apparatus. Since the memo function was used to enter the names of the patients, the measurement data were not mixed up. Since passwords were used for data management, patient's privacy could be protected during measurement. The measurement data could be graphically represented. Furthermore, the optical disk storing the data was portable, so that the data could be managed or analyzed by another PC.

What is claimed is:

1. An enzyme electrode comprising an electrode on an insulating substrate, an immobilized enzyme layer on the electrode and a permeation restricting layer on the immobilized enzyme layer, said permeation restricting layer consisting essentially of a polymer in which a pendant group containing at least a fluoroalkylene block is attached to a non-fluorinated vinyl polymer.

2. An enzyme electrode as claimed in claim 1 where the vinyl polymer is a homopolymer or copolymer of one or more monomers selected from the group consisting of unsaturated hydrocarbons, unsaturated carboxylic acids and unsaturated alcohols.

3. An enzyme electrode as claimed in claim 1 where the vinyl polymer is a polycarboxylic acid.

4. An enzyme electrode as claimed in claim 1 where the fluoroalkylene block is attached to the vinyl polymer via an ester group.

5. An enzyme electrode as claimed in claim 1 where the fluorine content represented by $x/(x+y)$ in the pendant group is 0.3 to 1, where x and y are the numbers of fluorine and hydrogen atoms in the pendant group, respectively.

6. An enzyme electrode as claimed in claim 1 where the pendant group has 3 to 15 carbon atoms.

7. An enzyme electrode as claimed in claim 1 where the permeation restricting layer has a thickness of 0.01 to 3 $\mu$m.

8. A biosensor comprising an enzyme electrode as claimed in claim 1 as a working electrode.

9. A biosensor as claimed in claim 8, which is used for measuring a glucose concentration in urine.

10. A measuring apparatus comprising a biosensor as claimed in claim 8 and a data indicator indicating an electric signal from the biosensor.

11. A measuring ap atus comprising a biosensor as claimed in claim 8, an electrochemical measuring circuit receiving an electric signal from the biosensor, a data processor calculating a measured value based on the electric signal, and a data indicator indicating the measured value.

12. A measuring apparatus as claimed in claim 11 where the data processor comprises all or some of the following means;

(a) a timer, (b) a time setting means for setting a time and a time indicator indicating a time at the time set by the time setting means, (c) an operation guide means describing operation instructions for the measuring apparatus, (d) a measured-value storing means for storing a calculated measured value, (e) a password registration means for registering a password for a user of the measuring apparatus, (f) a memo registration means for registering a memo, (g) an operation indicator for detecting malfunction in the measuring apparatus, (h) a calibration-timing indicator for detecting and indicating a calibration timing for the enzyme electrode, (i) an electrode-replacement-timing indicator for detecting and indicating a replacement timing for the enzyme electrode, (j) an abnormal-current indicator for detecting and indicating an abnormal current, and (k) an electrode calibrator for calibrating the enzyme electrode.

13. An enzyme electrode comprising an electrode on an insulating substrate, an immobilized enzyme layer on the electrode and a permeation restricting layer on the immobilized enzyme layer, said permeation restricting layer mainly consisting of a polycarboxylic acid (A) fluoroalcohol ester.

14. An enzyme electrode as claimed in claim 13 where the polycarboxylic acid (A) is polymethacrylic acid, polyacrylic acid or a copolymer of acrylic acid and methacrylic acid.

15. An enzyme electrode as claimed in claim 13 where the fluorine content represented by $x/(x+y)$ in the polycarboxylic acid (A) fluoroalcohol ester is 0.3 to 1, where x and y are the numbers of fluorine and hydrogen atoms in the fluoroalcohol ester, respectively.

16. An enzyme electrode as claimed in claim 13 where the fluoroalcohol moiety in the polycarboxylic acid (A) fluoroalcohol ester has 3 to 15 carbon atoms.

17. An enzyme electrode as claimed in claim 13 where the permeation restricting layer has a thickness of 0.01 to 3 µm.

18. A biosensor comprising an enzyme electrode as claimed in claim 13 as a working electrode.

19. A biosensor as claimed in claim 18, which is used for measuring a glucose concentration in urine.

20. An enzyme electrode comprising an electrode on an insulating substrate, an immobilized enzyme layer on the electrode and a permeation restricting layer on the immobilized enzyme layer, said permeation restricting layer comprising a polycarboxylic acid (A) fluoroalcohol ester and a polycarboxylic acid (B) alkylalcohol ester.

21. An enzyme electrode as claimed in claim 20 where the polycarboxylic acid (A) is polymethacrylic acid, polyacrylic acid or a copolymer of acrylic acid and methacrylic acid.

22. An enzyme electrode as claimed in claim 20 where the fluorine content represented by x/(x+y) in the polycarboxylic acid (A) fluoroalcohol ester is 0.3 to 1, where x and y are the numbers of fluorine and hydrogen atoms in the fluoroalcohol ester, respectively.

23. An enzyme electrode as claimed in claim 20 where the fluoroalcohol moiety in the polycarboxylic acid (A) fluoroalcohol ester has 3 to 15 carbon atoms.

24. An enzyme electrode as claimed in claim 20 where the polycarboxylic acid (B) is polymethacrylic acid, polyacrylic acid or a copolymer of acrylic acid and methacrylic acid.

25. An enzyme electrode as claimed in claim 20 where the polycarboxylic acid (B) alkylalcohol ester is the polycarboxylic acid (B) whose carboxyl groups are at least partially esterified with an alkylalcohol having 2 to 10 carbon atoms.

26. An enzyme electrode as claimed in claim 20 where the polycarboxylic acid (B) alkylalcohol ester is cyclohexyl polymethacrylate.

27. An enzyme electrode as claimed in claim 20 where the permeation restricting layer has a thickness of 0.01 to 3 µm.

28. A biosensor comprising an enzyme electrode as claimed in claim 20 as a working electrode.

29. A biosensor as claimed in claim 28 which is used for measuring a glucose concentration in urine.

30. An enzyme electrode comprising an electrode on an insulating substrate, an immobilized enzyme layer on the electrode and a permeation restricting layer on the immobilized enzyme layer, said permeation restricting layer consisting essentially of a polycarboxylate comprising alkylalcohol ester and fluoroalcohol ester groups.

31. An enzyme electrode as claimed in claim 30 where the fluorine content represented by x/(x+y) in the fluoroalcohol ester group is 0.3 to 1, where x and y are the numbers of fluorine and hydrogen atoms in the fluoroalcohol ester group, respectively.

32. An enzyme electrode as claimed in claim 30 where the fluoroalcohol moiety in the fluoroalcohol ester group has 3 to 15 carbon atoms.

33. An enzyme electrode as claimed in claim 30 where the alkylalcohol ester group has 2 to 10 carbon atoms.

34. An enzyme electrode as claimed in claim 30 where the alkylalcohol ester group is a cyclohexyl polymethacrylate moiety.

35. An enzyme electrode as claimed in claim 30 where the permeation restricting layer has a thickness of 0.01 to 3 µm.

36. A biosensor comprising an enzyme electrode as claimed in claim 30 as a working electrode.

37. A biosensor as claimed in claim 36, which is used for measuring a glucose concentration in urine.

38. An enzyme electrode comprising:

an electrode on an insulating substrate, an electrode protection layer comprising an urea compound covering at least a part of the electrode, and an immobilized enzyme layer covering the electrode and the electrode protection layer.

39. An enzyme electrode as claimed in claim 38 where the urea compound is urea or thiourea.

40. An enzyme electrode as claimed in claim 38 where the electrode is a platinum electrode.

41. An enzyme electrode as claimed in claim 38 where the electrode protection layer is formed by soaking the insulating substrate with the electrode into a mixed solution comprising a supporting electrolyte and an urea compound while applying electricity.

42. An enzyme electrode as claimed in claim 41 where the mixed solution contains 0.1 mM to 6.7 M of urea and 0.1 mM to 2M of sodium chloride.

43. An enzyme electrode as claimed in claim 38 where a permeation restricting layer consisting essentially of a polymer in which a pendant group containing at least a fluoroalkylene block is attached to a non-fluorinated vinyl polymer is formed on the immobilized enzyme layer.

44. An enzyme electrode as claimed in claim 43 where the polymer is a fluoroalcohol polycarboxylate.

45. A biosensor comprising an enzyme electrode as claimed in claim 38 as a working electrode.

46. A biosensor as claimed in claim 45, which is used for measuring a glucose concentration in urine.

47. A method for manufacturing an enzyme electrode comprising the steps of:

forming an electrode on an insulating substrate, applying a first liquid containing an enzyme to the electrode directly or via another layer and then drying it to form an immobilized enzyme layer, and applying a second liquid containing a polymer in which a pendant group having at least a fluoroalkylene block is attached to a non-fluorinated vinyl polymer, to the immobilized enzyme layer directly or via another layer and then drying it to form a permeation restricting layer.

48. A method for manufacturing an enzyme electrode as claimed in claim 47 where the second liquid is applied by spin coating.

49. A method for manufacturing an enzyme electrode as claimed in claim 47 where the second liquid is applied by dipping and then the substrate is dried by nitrogen blowing.

50. A method for manufacturing an enzyme electrode as claimed in claim 47 where the permeation restricting layer has a thickness of 0.01 to 3 µm after drying.

51. A method for manufacturing an enzyme electrode comprising the steps of: forming an electrode on an insulating substrate surface, then applying electricity to the insulating substrate while being soaked in a mixed solution comprising a supporting electrolyte and an urea compound to cover at least a part of the electrode with an electrode protection layer comprising the urea compound, and applying an enzyme to the electrode.

52. A method for manufacturing an enzyme electrode as claimed in claim 51 where the supporting electrolyte is sodium chloride.

53. A method for manufacturing an enzyme electrode as claimed in claim 52 where the mixed solution contains 0.1 mM to 6.7 M of urea and 0.1 mM to 2M of sodium chloride.

* * * * *